US012394148B2

(12) United States Patent
Hershkovich et al.

(10) Patent No.: US 12,394,148 B2
(45) Date of Patent: Aug. 19, 2025

(54) METHODS, SYSTEMS, AND APPARATUSES FOR MANAGING TRANSDUCER ARRAY PLACEMENT

(71) Applicant: Novocure GmbH, Root (CH)

(72) Inventors: Hadas Sara Hershkovich, Haifa (IL); Zeev Bomzon, Haifa (IL); Gil Zigelman, Haifa (IL); Shira Luk-Zilberman, Haifa (IL); Ori Kook, Haifa (IL); Oren Ben Zion Bakalo, Haifa (IL)

(73) Assignee: Novocure GmbH, Baar (CH)

( * ) Notice: Subject to any disclaimer, the term of this patent is extended or adjusted under 35 U.S.C. 154(b) by 0 days.

(21) Appl. No.: 18/116,739

(22) Filed: Mar. 2, 2023

(65) Prior Publication Data

US 2023/0206548 A1 Jun. 29, 2023

Related U.S. Application Data

(63) Continuation of application No. 16/866,417, filed on May 4, 2020, now Pat. No. 11,620,789.

(60) Provisional application No. 62/842,674, filed on May 3, 2019.

(51) Int. Cl.
*G06T 17/00* (2006.01)
*A61N 1/40* (2006.01)

(52) U.S. Cl.
CPC ............... *G06T 17/00* (2013.01); *A61N 1/40* (2013.01); *G06T 2210/41* (2013.01)

(58) Field of Classification Search
None
See application file for complete search history.

(56) References Cited

U.S. PATENT DOCUMENTS

| 6,747,665 | B1 | 6/2004 | Stoval, III et al. |
| 7,565,205 | B2 | 7/2009 | Palti |
| 2006/0198555 | A1* | 9/2006 | Hosotsubo ............. G06T 11/60 382/162 |
| 2011/0106221 | A1 | 5/2011 | Neal, II et al. |
| 2011/0122068 | A1* | 5/2011 | Venon ................ G06F 3/04815 345/169 |
| 2012/0197086 | A1* | 8/2012 | Morris ............... A61B 1/00082 600/188 |
| 2012/0216617 | A1 | 8/2012 | Hoctor et al. |
| 2013/0101187 | A1* | 4/2013 | Sundar .................... G06T 7/246 382/128 |
| 2014/0200575 | A1 | 7/2014 | Spector |

(Continued)

FOREIGN PATENT DOCUMENTS

| JP | 2019-500179 A | 1/2019 |
| WO | 2017/072706 A1 | 5/2017 |

(Continued)

OTHER PUBLICATIONS

English Translation of Office Action issued in Japanese Application No. 2021-560069 dated Oct. 31, 2022.
Ballo, et al., "Correlation of Tumor Treating Fields Dosimetry to Survival Outcomes in Newly Diagnosed Glioblastoma: A Large-Scale Numerical Simulation-Based Analysis of Data from the Phase 3 EF-14 Randomized Trial," International Journal of Radiation Oncology, Biology, Physics, 2019; 104(5), pp. 1106-1113.

(Continued)

*Primary Examiner* — Anh-Tuan V Nguyen
(74) *Attorney, Agent, or Firm* — McCarter & English, LLP; Michael A. Sartori

(57) ABSTRACT

Methods, systems, and apparatuses are described for managing placement of transducer arrays on a subject/patient.

20 Claims, 17 Drawing Sheets

(56) References Cited

U.S. PATENT DOCUMENTS

| | | | |
|---|---|---|---|
| 2015/0288933 A1* | 10/2015 | Iversen | G06T 7/174 |
| | | | 348/14.07 |
| 2016/0331264 A1* | 11/2016 | Helms-Tillery | A61B 5/4005 |
| 2017/0049497 A1 | 2/2017 | Radecke | |
| 2017/0120041 A1* | 5/2017 | Wenger | A61B 5/24 |
| 2017/0178266 A1* | 6/2017 | Schmidt | G06F 40/134 |
| 2017/0193160 A1 | 7/2017 | Long et al. | |
| 2017/0352157 A1* | 12/2017 | Madabhushi | G16H 30/40 |
| 2018/0001075 A1 | 1/2018 | Kirson et al. | |
| 2018/0046758 A1* | 2/2018 | Gogin | G06F 21/6254 |
| 2019/0117956 A1 | 4/2019 | Wenger et al. | |
| 2019/0184204 A1 | 6/2019 | Ramamurthy | |
| 2019/0314631 A1 | 10/2019 | Wong et al. | |
| 2020/0016396 A1 | 1/2020 | Yoo | |
| 2020/0214570 A1 | 7/2020 | Kim | |
| 2020/0226748 A1* | 7/2020 | Kaufman | G06F 18/254 |
| 2021/0124042 A1 | 4/2021 | Fish et al. | |
| 2021/0132223 A1 | 5/2021 | Hennersperger et al. | |
| 2021/0233303 A1 | 7/2021 | Takahashi | |

FOREIGN PATENT DOCUMENTS

| | | |
|---|---|---|
| WO | WO-2018/002879 A1 | 1/2018 |
| WO | WO-2018057953 A2 | 3/2018 |

OTHER PUBLICATIONS

International Search Report mailed Aug. 4, 2020 by the International Search Authority for International Application No. PCT/IB2020/000345, filed on May 5, 2020 (12 pages).

Wenger et al. "A Review on Tumor-Treating Fields (TTFields): Clinical Implications Inferred From Computational Modeling", IEEE reviews in biomedical engineering, vol. 11, Jul. 24, 2018.

Chaudhry et al., NovoTTFTTM-100A System (Tumor Treating Fields) Transducer Array Layout Planning for Glioblastoma: A NovoTal TM System User Study, 2015, World Journal of Surgical Oncology, 13:316 (Year: 2015).

\* cited by examiner

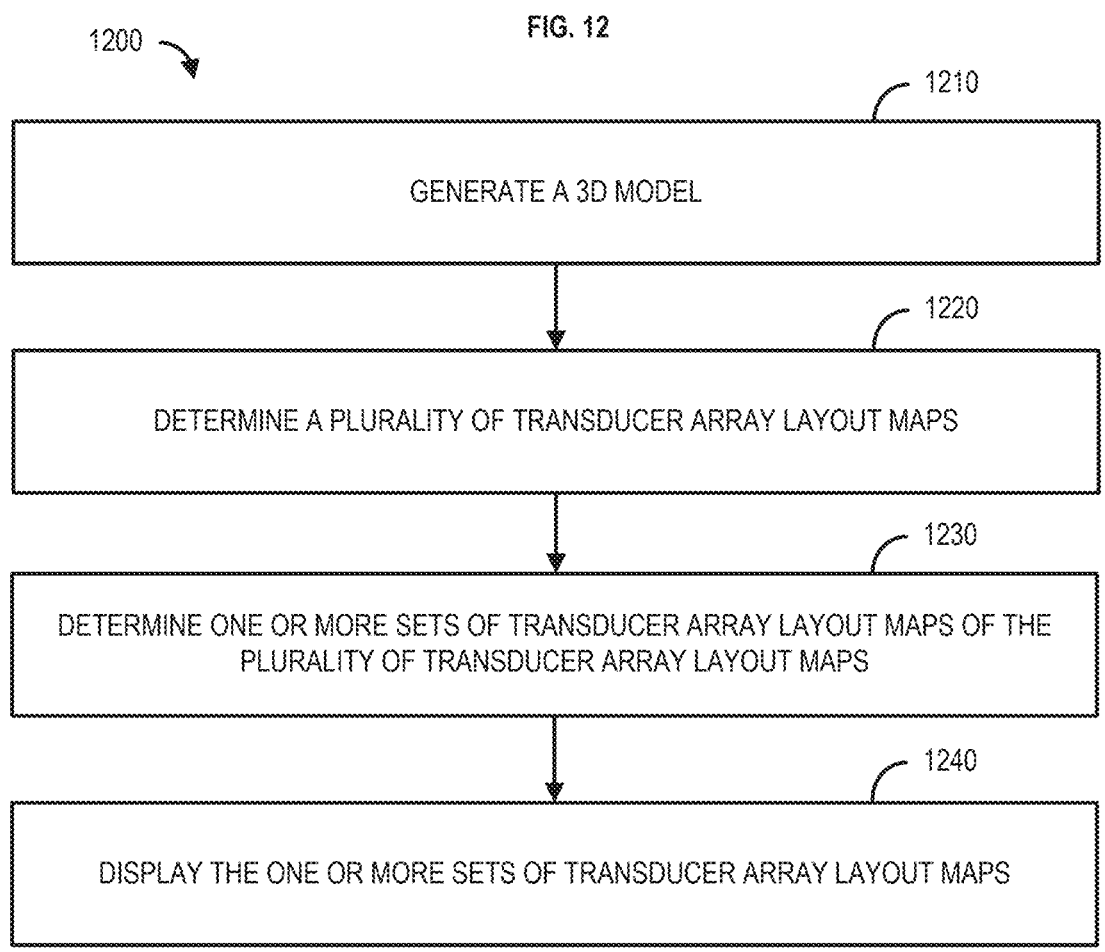

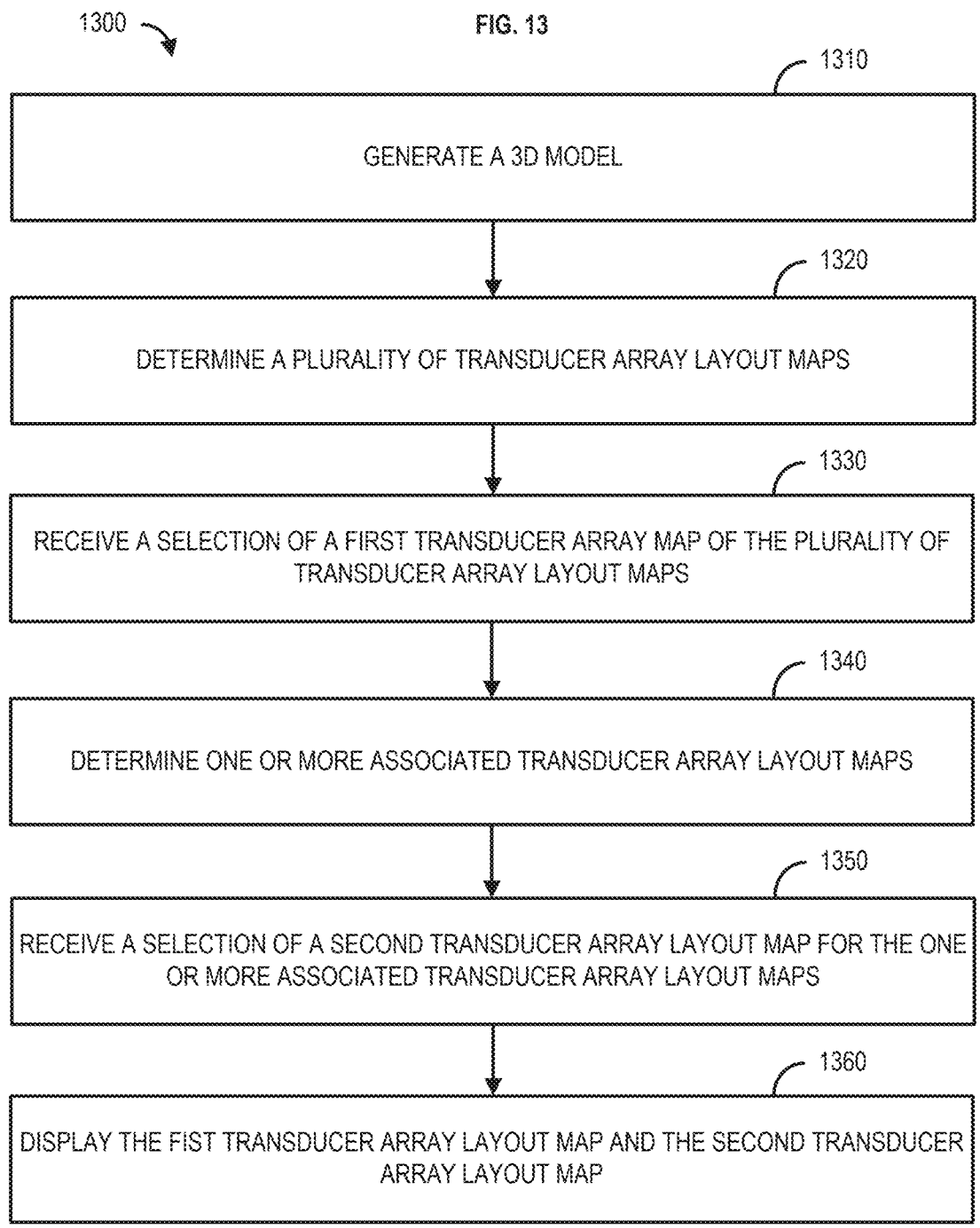

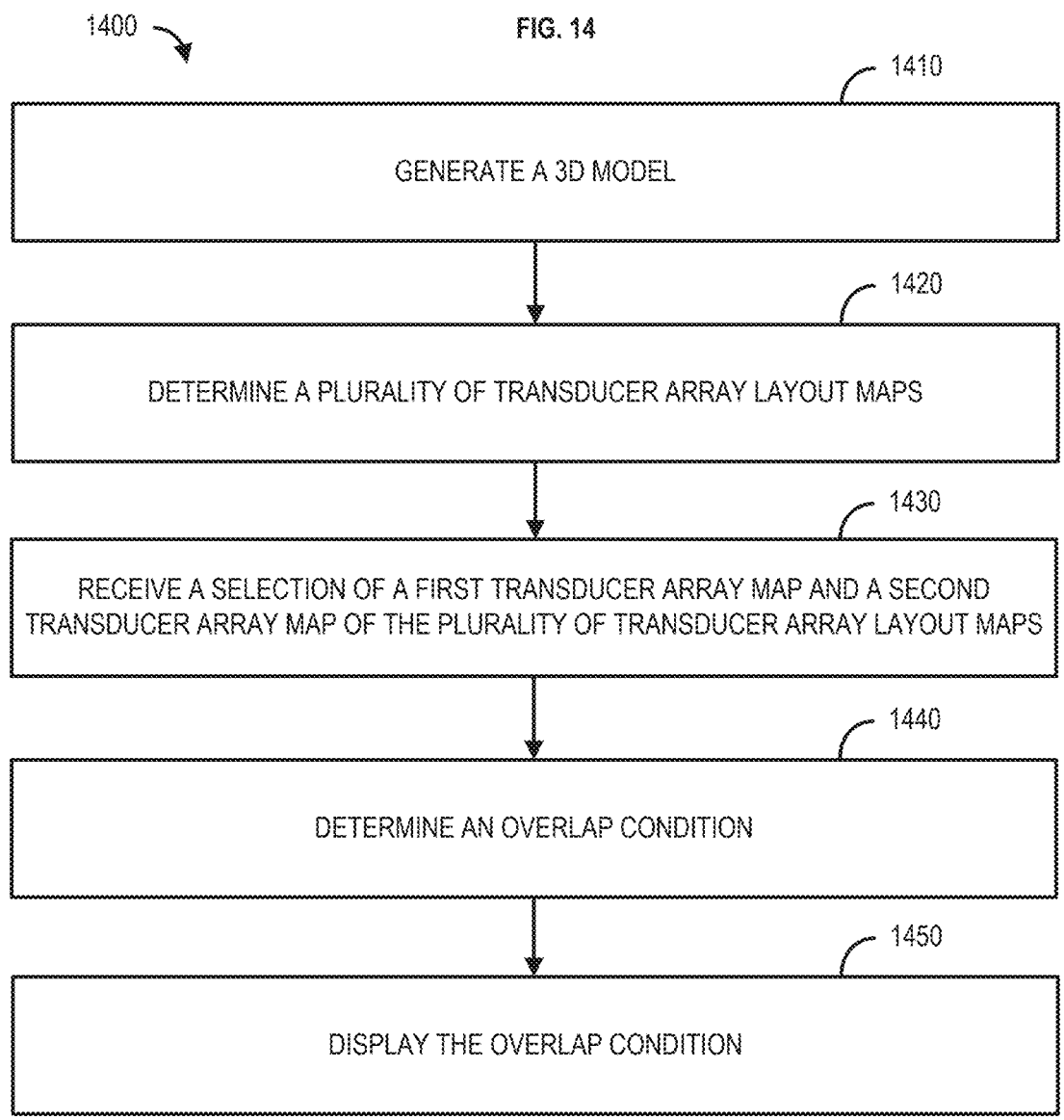

METHODS, SYSTEMS, AND APPARATUSES FOR MANAGING TRANSDUCER ARRAY PLACEMENT

CROSS REFERENCE TO RELATED PATENT APPLICATION

This application is a continuation of U.S. application Ser. No. 16/866,417 filed May 4, 2020, which claims priority to U.S. Provisional Application No. 62/842,674 filed May 3, 2019, both of which are incorporated herein by reference in their entirety.

BACKGROUND

Tumor Treating Fields, or TTFields, are low intensity (e.g., 1-3 V/cm) alternating electrical fields within the intermediate frequency range (100-300 kHz). This non-invasive treatment targets solid tumors and is described in U.S. Pat. No. 7,565,205, which is incorporated herein by reference in its entirety. TTFields disrupt cell division through physical interactions with key molecules during mitosis. TTFields therapy is an approved mono-treatment for recurrent glioblastoma, and an approved combination therapy with chemotherapy for newly diagnosed patients. These electrical fields are induced non-invasively by transducer arrays (i.e., arrays of electrodes) placed directly on the patient's scalp. TTFields also appear to be beneficial for treating tumors in other parts of the body.

The efficacy of TTFields therapy increases as the intensity of the electric field increases. Changing the positioning of the transducer arrays on a patient's scalp (and/or other parts of the body) affects the intensity of the electric field in a target region. Determining how the positioning of transducer arrays may be changed while maintaining a target intensity of the electric field in the target region is difficult, labor-intensive, and time-consuming process.

SUMMARY

Described are methods comprising generating a three-dimensional (3D) model of a portion of the subject's body, determining, based on the 3D model and a plurality of simulated electrical field distributions, a plurality of transducer array layout maps, determining, from the plurality of transducer array layout maps, one or more sets of transducer array layout maps, wherein each set of transducer array layout maps represents at least two transducer array layout maps with non-overlapping positions of a plurality of pairs of positions for transducer array placement, wherein the at least two transducer array layout maps satisfy a criterion, and causing display of the one or more sets of transducer array layout maps.

Also described are methods comprising generating a three-dimensional (3D) model of a portion of the subject's body, determining, based on the 3D model and a plurality of simulated electrical field distributions, a plurality of transducer array layout maps, receiving a selection of a first transducer array layout map of the plurality of transducer array layout maps, wherein the first transducer array layout map satisfies a criterion, determining, from the plurality of transducer array layout maps, one or more associated transducer array layout maps, wherein each associated transducer array layout map comprises positions for transducer array placement that do not overlap positions for transducer array placement of the first transducer array layout map, wherein each associated transducer array layout map satisfies the criterion, receiving a selection of a second transducer array layout map from the plurality of associated transducer array layout maps, and causing display of the first transducer array layout map and the second transducer array layout map.

Also described are methods comprising generating a three-dimensional (3D) model of a portion of the subject's body, determining, based on the 3D model and a plurality of simulated electrical field distributions, a plurality of transducer array layout maps, receiving a selection of a first transducer array layout map and a second transducer array layout map of the plurality of transducer array layout maps, determining, based on the first transducer array layout map and the second transducer array layout map, an overlap condition, and causing display of the overlap condition.

Additional advantages will be set forth in part in the description which follows or may be learned by practice. The advantages will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE DRAWINGS

To easily identify the discussion of any particular element or act, the most significant digit or digits in a reference number refer to the figure number in which that element is first introduced.

FIG. 12 shows an example method for managing transducer array placement.

FIG. 13 shows an example method for managing transducer array placement.

FIG. 14 shows an example method for managing transducer array placement.

DETAILED DESCRIPTION

Figure 1:
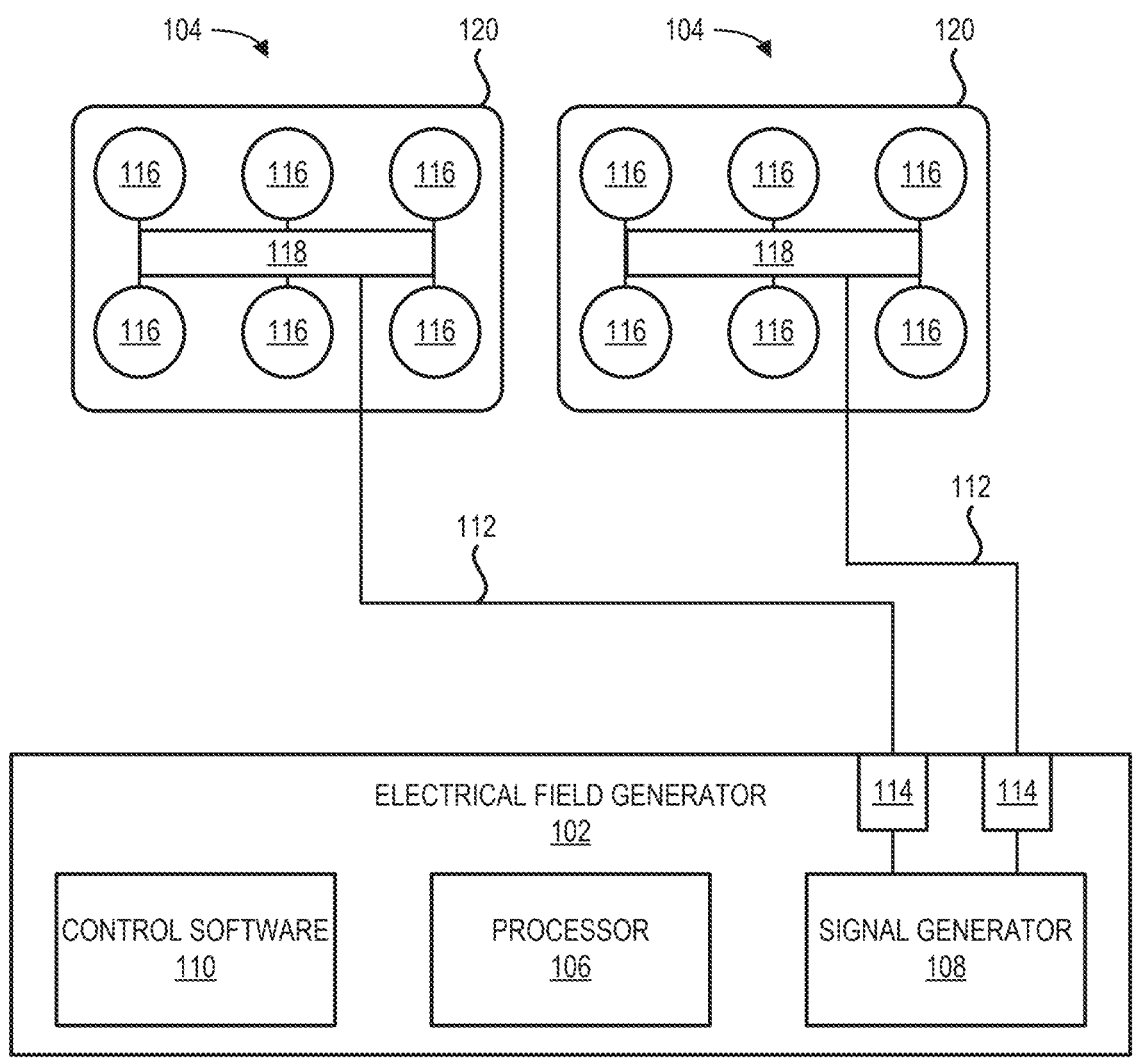
FIG. 1 shows an example apparatus for electrotherapeutic treatment.

Before the present methods and systems are disclosed and described, it is to be understood that the methods and systems are not limited to specific methods, specific components, or to particular implementations. It is also to be understood that the terminology used herein is for the purpose of describing particular embodiments only and is not intended to be limiting.

As used in the specification and the appended claims, the singular forms "a," "an" and "the" include plural referents unless the context clearly dictates otherwise. Ranges may be expressed herein as from "about" one particular value, and/or to "about" another particular value. When such a range is expressed, another embodiment includes—from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other components, integers or steps. "Exemplary" means "an example of" and is not intended to convey an indication of a preferred or ideal embodiment. "Such as" is not used in a restrictive sense, but for explanatory purposes.

Disclosed are components that can be used to perform the disclosed methods and systems. These and other components are disclosed herein, and it is understood that when combinations, subsets, interactions, groups, etc. of these components are disclosed that while specific reference of each various individual and collective combinations and permutation of these may not be explicitly disclosed, each is specifically contemplated and described herein, for all methods and systems. This applies to all aspects of this application including, but not limited to, steps in disclosed methods. Thus, if there are a variety of additional steps that can be performed it is understood that each of these additional steps can be performed with any specific embodiment or combination of embodiments of the disclosed methods.

The present methods and systems may be understood more readily by reference to the following detailed description of preferred embodiments and the examples included therein and to the Figures and their previous and following description.

As will be appreciated by one skilled in the art, the methods and systems may take the form of an entirely hardware embodiment, an entirely software embodiment, or an embodiment combining software and hardware aspects. Furthermore, the methods and systems may take the form of a computer program product on a computer-readable storage medium having computer-readable program instructions (e.g., computer software) embodied in the storage medium. More particularly, the present methods and systems may take the form of web-implemented computer software. Any suitable computer-readable storage medium may be utilized including hard disks, CD-ROMs, optical storage devices, or magnetic storage devices.

Embodiments of the methods and systems are described below with reference to block diagrams and flowchart illustrations of methods, systems, apparatuses and computer program products. It will be understood that each block of the block diagrams and flowchart illustrations, and combinations of blocks in the block diagrams and flowchart illustrations, respectively, can be implemented by computer program instructions. These computer program instructions may be loaded onto a general purpose computer, special purpose computer, or other programmable data processing apparatus to produce a machine, such that the instructions which execute on the computer or other programmable data processing apparatus create a means for implementing the functions specified in the flowchart block or blocks.

These computer program instructions may also be stored in a computer-readable memory that can direct a computer or other programmable data processing apparatus to function in a particular manner, such that the instructions stored in the computer-readable memory produce an article of manufacture including computer-readable instructions for implementing the function specified in the flowchart block or blocks. The computer program instructions may also be loaded onto a computer or other programmable data processing apparatus to cause a series of operational steps to be performed on the computer or other programmable apparatus to produce a computer-implemented process such that the instructions that execute on the computer or other programmable apparatus provide steps for implementing the functions specified in the flowchart block or blocks.

Accordingly, blocks of the block diagrams and flowchart illustrations support combinations of means for performing the specified functions, combinations of steps for performing the specified functions and program instruction means for performing the specified functions. It will also be understood that each block of the block diagrams and flowchart illustrations, and combinations of blocks in the block diagrams and flowchart illustrations, can be implemented by special purpose hardware-based computer systems that perform the specified functions or steps, or combinations of special purpose hardware and computer instructions.

TTFields, also referred to herein as alternating electrical fields, are established as an anti-mitotic cancer treatment modality because they interfere with proper micro-tubule assembly during metaphase and eventually destroy the cells during telophase and cytokinesis. The efficacy increases with increasing field strength and the optimal frequency is cancer cell line dependent with 200 kHz being the frequency for which inhibition of glioma cells growth caused by TTFields is highest. For cancer treatment, non-invasive devices were developed with capacitively coupled transducers that are placed directly at the skin region close to the tumor, for example, for patients with Glioblastoma Multiforme (GBM), the most common primary, malignant brain tumor in humans.

Because the effect of TTFields is directional with cells dividing parallel to the field affected more than cells dividing in other directions, and because cells divide in all directions, TTFields are typically delivered through two pairs of transducer arrays that generate perpendicular fields within the treated tumor. More specifically, one pair of transducer arrays may be located to the left and right (LR) of the tumor, and the other pair of transducer arrays may be located anterior and posterior (AP) to the tumor. Cycling the field between these two directions (i.e., LR and AP) ensures that a maximal range of cell orientations is targeted. Other positions of transducer arrays are contemplated beyond perpendicular fields. In an embodiment, asymmetric positioning of three transducer arrays is contemplated wherein one pair of the three transducer arrays may deliver alternating electrical fields and then another pair of the three transducer arrays may deliver the alternating electrical fields, and the remaining pair of the three transducer arrays may deliver the alternating electrical fields.

In-vivo and in-vitro studies show that the efficacy of TTFields therapy increases as the intensity of the electrical field increases. Therefore, optimizing array placement on the patient's scalp to increase the intensity in the diseased region of the brain is standard practice for the Optune system. Array placement optimization may be performed by "rule of thumb" (e.g., placing the arrays on the scalp as close to the tumor as possible) measurements describing the geometry of the patient's head, tumor dimensions, and/or tumor location. Measurements used as input may be derived from imaging data. Imaging data is intended to include any type of visual data, such as for example, single-photon emission computed tomography (SPECT) image data, x-ray computed tomography (x-ray CT) data, magnetic resonance imaging (MRI) data, positron emission tomography (PET) data, data that can be captured by an optical instrument (e.g., a photographic camera, a charge-coupled device (CCD) camera, an infrared camera, etc.), and the like. In certain implementations, image data may include 3D data obtained from or generated by a 3D scanner (e.g., point cloud data). Optimization can rely on an understanding of how the electrical field distributes within the head as a function of the positions of the array and, in some aspects, take account for variations in the electrical property distributions within the heads of different patients. A plurality of transducer array maps that indicate optimized positioning for transducer arrays on a patient's body that satisfy various criterion (e.g., provide a minimum and/or maximum strength of an electric field within a region-of-interest (ROI), power density within the ROI, etc.) may be determined.

Since, the positioning of the transducer arrays on a patient's scalp (and/or other parts of the body) affects the intensity of the electric field in a ROI and/or target region, transducer array maps that enable the positioning of transducer arrays to be changed while maintaining a target intensity of the electric field in the ROI and/or target region may be determined.

FIG. 1 shows an example apparatus 100 for electrotherapeutic treatment. Generally, the apparatus 100 may be a portable, battery or power supply operated device which produces alternating electrical fields within the body by means of non-invasive surface transducer arrays. The apparatus 100 may comprise an electrical field generator 102 and one or more transducer arrays 104. The apparatus 100 may be configured to generate tumor treatment fields (TTFields) (e.g., at 150 kHz) via the electrical field generator 102 and deliver the TTFields to an area of the body through the one or more transducer arrays 104. The electrical field generator 102 may be a battery and/or power supply operated device. In an embodiment, the one or more transducer arrays 104 are uniformly shaped. In an embodiment, the one or more transducer arrays 104 are not uniformly shaped.

The electrical field generator 102 may comprise a processor 106 in communication with a signal generator 108. The electrical field generator 102 may comprise control software 110 configured for controlling the performance of the processor 106 and the signal generator 108.

The signal generator 108 may generate one or more electric signals in the shape of waveforms or trains of pulses. The signal generator 108 may be configured to generate an alternating voltage waveform at frequencies in the range from about 50 KHz to about 500 KHz (preferably from about 100 KHz to about 300 KHz) (e.g., the TTFields). The voltages are such that the electrical field intensity in tissue to be treated is in the range of about 0.1 V/cm to about 10 V/cm.

One or more outputs 114 of the electrical field generator 102 may be coupled to one or more conductive leads 112 that are attached at one end thereof to the signal generator 108. The opposite ends of the conductive leads 112 are connected to the one or more transducer arrays 104 that are activated by the electric signals (e.g., waveforms). The conductive leads 112 may comprise standard isolated conductors with a flexible metal shield and may be grounded to prevent the spread of the electrical field generated by the conductive leads 112. The one or more outputs 114 may be operated sequentially. Output parameters of the signal generator 108 may comprise, for example, an intensity of the field, a frequency of the waves (e.g., treatment frequency), and a maximum allowable temperature of the one or more transducer arrays 104. The output parameters may be set and/or determined by the control software 110 in conjunction with the processor 106. After determining a desired (e.g., optimal) treatment frequency, the control software 110 may cause the processor 106 to send a control signal the signal generator 108 that causes the signal generator 108 to output the desired treatment frequency to the one or more transducer arrays 104.

The one or more transducer arrays 104 may be configured in a variety of shapes and positions so as to generate an electrical field of the desired configuration, direction and intensity at a target volume so as to focus treatment. The one or more transducer arrays 104 may be configured to deliver two perpendicular field directions through a volume of interest.

The one or more transducer arrays 104 arrays may comprise one or more electrodes 116. The one or more electrodes 116 may be made from any material with a high dielectric constant. The one or more electrodes 116 may comprise, for example, one or more insulated ceramic discs. The electrodes 116 may be biocompatible and coupled to a flexible circuit board 118. The electrodes 116 may be configured so as to not come into direct contact with the skin as the electrodes 116 are separated from the skin by a layer of conductive hydrogel (not shown) (similar to that found on electrocardiogram pads).

The electrodes 116, the hydrogel, and the flexible circuit board 118 may be attached to a hypo-allergenic medical adhesive bandage 120 to keep the one or more transducer arrays 104 in place on the body and in continuous direct contact with the skin. Each transducer array 104 may comprise one or more thermistors (not shown), for example 8 thermistors, (accuracy ±1° C.) to measure skin temperature beneath the transducer arrays 104. The thermistors may be configured to measure skin temperature periodically, for example, every second. The thermistors may be read by the control software 110 while the TTFields are not being delivered in order to avoid any interference with the temperature measurements.

If the temperature measured is below a pre-set maximum temperature (Tmax), for example 38.5-40.0° C.±0.3° C., between two subsequent measures, the control software 110 can increase current until the current reaches maximal treatment current (for example, 4 Amps peak-to-peak). If the temperature reaches Tmax+0.3° C. and continues to rise, the control software 110 can lower the current. If the temperature rises to 41° C., the control software 110 can shut off the TTFields therapy and an overheating alarm can be triggered.

Figure 2:
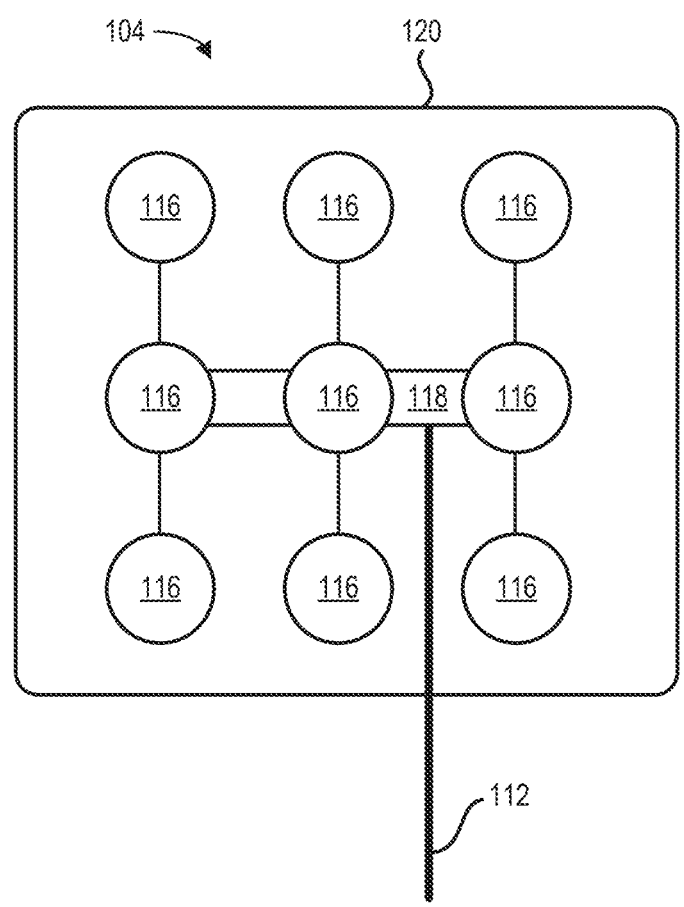
FIG. 2 shows an example transducer array.

The one or more transducer arrays 104 may vary in size and may comprise varying numbers of electrodes 116, based on patient body sizes and/or different therapeutic treatments. For example, in the context of the chest of a patient, small transducer arrays may comprise 13 electrodes each, and large transducer arrays may comprise 20 electrodes each, with the electrodes serially interconnected in each array. For example, as shown in FIG. 2, in the context of the head of a patient, each transducer array may comprise 9 electrodes each, with the electrodes serially interconnected in each array.

A status of the apparatus 100 and monitored parameters may be stored a memory (not shown) and can be transferred to a computing device over a wired or wireless connection. The apparatus 100 may comprise a display (not shown) for displaying visual indicators, such as, power on, treatment on, alarms, and low battery.

Figure 3A:
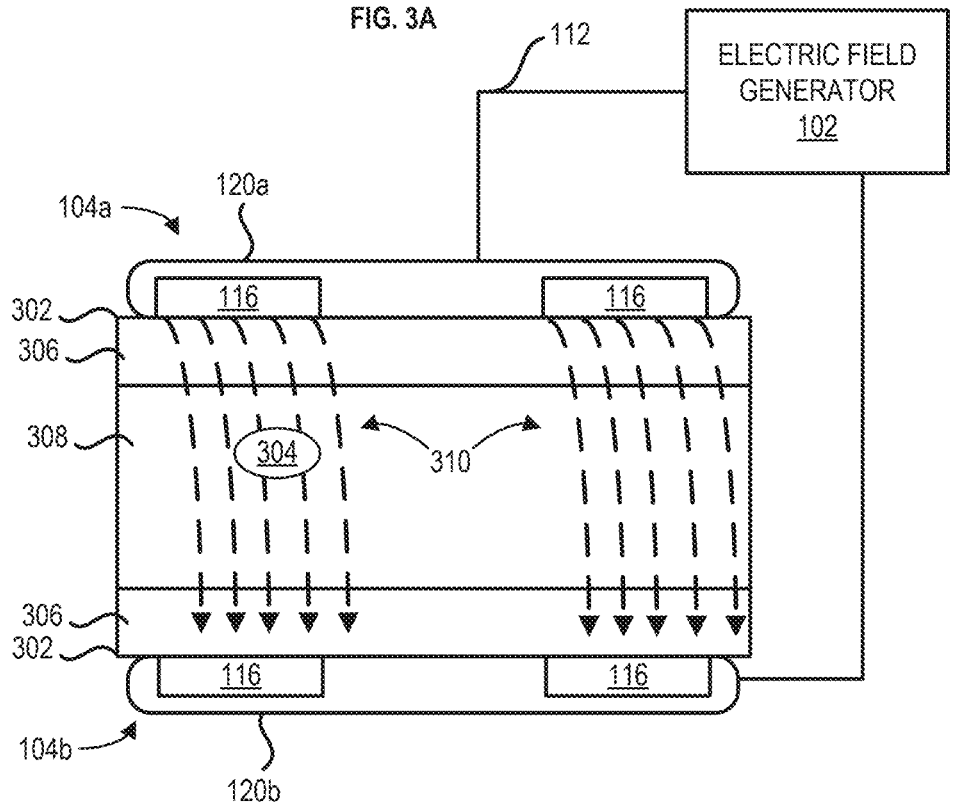
FIG. 3A and FIG. 3B illustrate an example application of the apparatus for electrotherapeutic treatment.
Figure 3B:
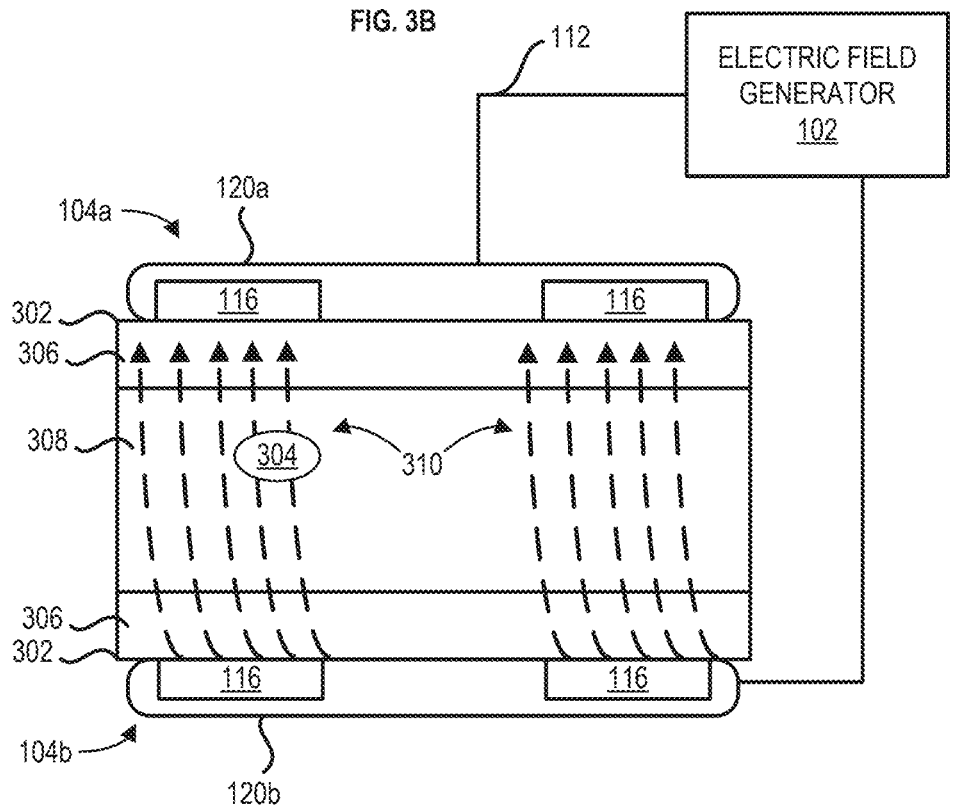

FIG. 3A and FIG. 3B illustrate an example application of the apparatus 100. A transducer array 104a and a transducer array 104b are shown, each incorporated into a hypo-allergenic medical adhesive bandage 120a and 120b, respectively. The hypo-allergenic medical adhesive bandages 120a and 120b are applied to skin surface 302. A tumor 304 is located below the skin surface 302 and bone tissue 306 and is located within brain tissue 308. The electrical field generator 102 causes the transducer array 104a and the transducer array 104b to generate alternating electrical fields 310 within the brain tissue 308 that disrupt rapid cell division exhibited by cancer cells of the tumor 304. The alternating electrical fields 310 have been shown in non-clinical experiments to arrest the proliferation of tumor cells and/or to destroy them. Use of the alternating electrical fields 310 takes advantage of the special characteristics, geometrical shape, and rate of dividing cancer cells, which make them susceptible to the effects of the alternating electrical fields 310. The alternating electrical fields 310 alter their polarity at an intermediate frequency (on the order of 100-300 kHz). The frequency used for a particular treatment may be specific to the cell type being treated (e.g., 150 kHz for MPM). The alternating electrical fields 310 have been shown to disrupt mitotic spindle microtubule assembly and to lead to dielectrophoretic dislocation of intracellular macromolecules and organelles during cytokinesis. These processes lead to physical disruption of the cell membrane and to programmed cell death (apoptosis).

Because the effect of the alternating electrical fields 310 is directional with cells dividing parallel to the field affected more than cells dividing in other directions, and because cells divide in all directions, alternating electrical fields 310 may be delivered through two pairs of transducer arrays 104 that generate perpendicular fields within the treated tumor. More specifically, one pair of transducer arrays 104 may be located to the left and right (LR) of the tumor, and the other pair of transducer arrays 104 may be located anterior and posterior (AP) to the tumor. Cycling the alternating electrical fields 310 between these two directions (e.g., LR and AP) ensures that a maximal range of cell orientations is targeted. In an embodiment, the alternating electrical fields 310 may be delivered according to a symmetric setup of transducer arrays 104 (e.g., four total transducer arrays 104, two matched pairs). In another embodiment, the alternating electrical fields 310 may be delivered according to an asymmetric setup of transducer arrays 104 (e.g., three total transducer arrays 104). An asymmetric setup of transducer arrays 104 may engage two of the three transducer arrays 104 to deliver the alternating electrical fields 310 and then switch to another two of the three transducer arrays 104 to deliver the alternating electrical fields 310, and the like.

In-vivo and in-vitro studies show that the efficacy of TTFields therapy increases as the intensity of the electrical field increases. The methods, systems, and apparatuses described are configured for optimizing array placement on the patient's scalp to increase the intensity in the diseased region of the brain.

Figure 4A:
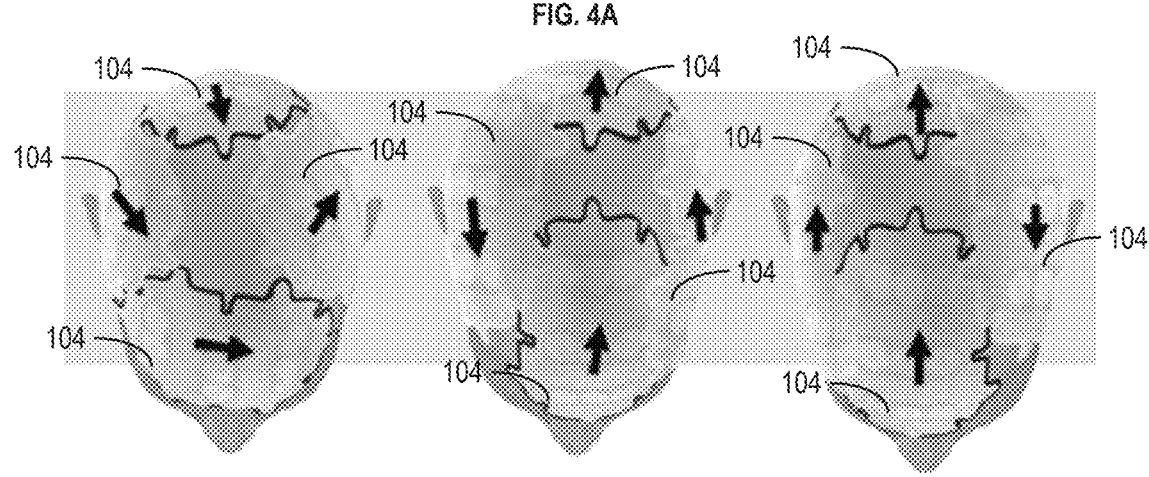
FIG. 4A shows transducer arrays placed on a patient's head.
Figure 4B:
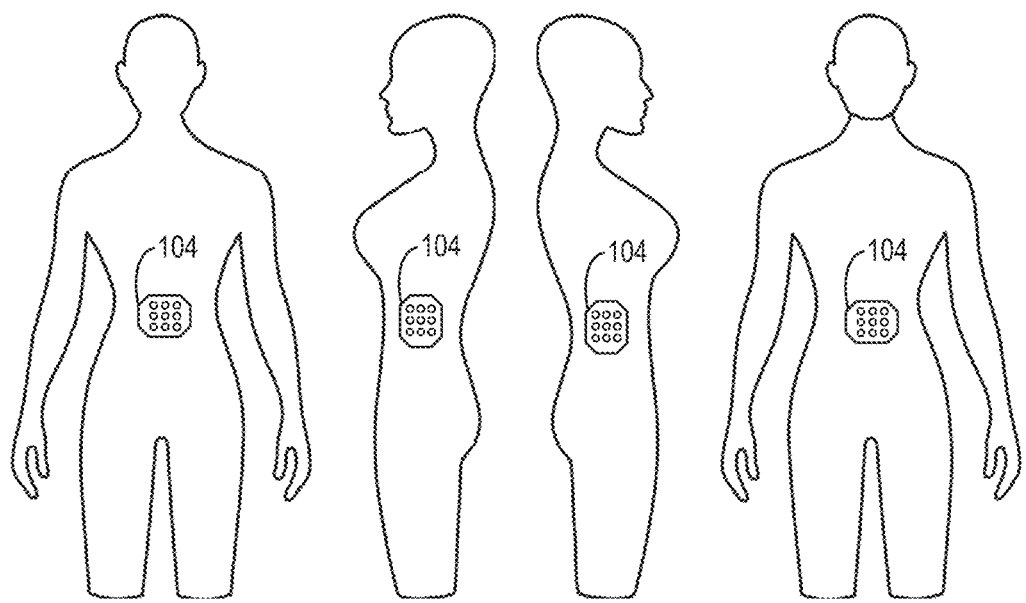
FIG. 4B shows transducer arrays placed on a patient's abdomen.
Figure 5A:
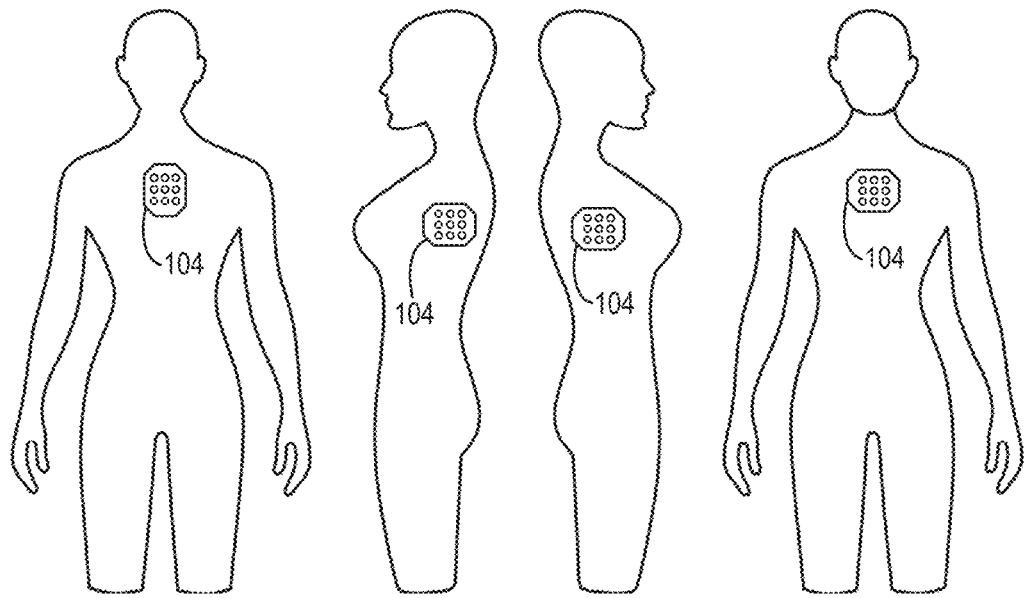
FIG. 5A, the transducer arrays placed on a patient's torso.
Figure 5B:
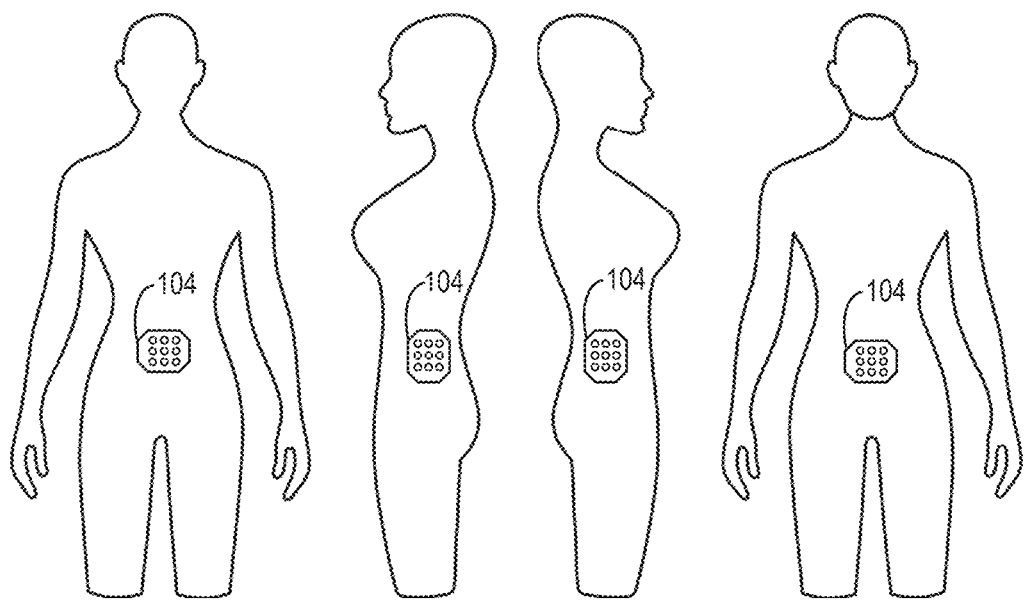
FIG. 5B shows transducer arrays placed on a patient's pelvis

As shown in FIG. 4A, the transducer arrays 104 may be placed on a patient's head. As shown in FIG. 4B, the transducer arrays 104 may be placed on a patient's abdomen. As shown in FIG. 5A, the transducer arrays 104 may be placed on a patient's torso. As shown in FIG. 5B, the transducer arrays 104 may be placed on a patient's pelvis. Placement of the transducer arrays 104 on other portions of a patient's body (e.g., arm, leg, etc.) is specifically contemplated.

Figure 6:
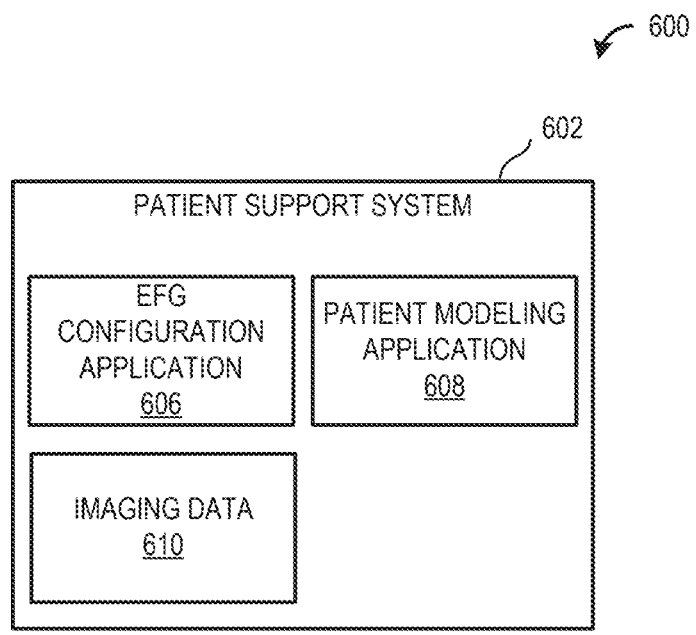
FIG. 6 is a block diagram of a system for managing transducer array placement.

FIG. 6 is a block diagram depicting non-limiting examples of a system 600 comprising a patient support system 602. The patient support system 602 can comprise one or multiple computers configured to operate and/or store an electrical field generator (EFG) configuration application 606, a patient modeling application 608, and/or imaging data 610. The patient support system 602 can comprise for example, a computing device. The patient support system 602 can comprise for example, a laptop computer, a desktop computer, a mobile phone (e.g., smartphone), a tablet, and the like.

The patient modeling application 608 may be configured to generate a three dimensional model of a portion of a body of a patient (e.g., a patient model) according to the imaging data 610. The imaging data 610 may comprise any type of visual data, such as for example, single-photon emission computed tomography (SPECT) image data, x-ray computed tomography (x-ray CT) data, magnetic resonance imaging (MRI) data, positron emission tomography (PET) data, data that can be captured by an optical instrument (e.g., a photographic camera, a charge-coupled device (CCD) camera, an infrared camera, etc.), and the like. In certain implementations, image data may include 3D data obtained from or generated by a 3D scanner (e.g., point cloud data). The patient modeling application 608 may also be configured to generate a three-dimensional array layout map based on the patient model and one or more electrical field simulations.

Figure 7:
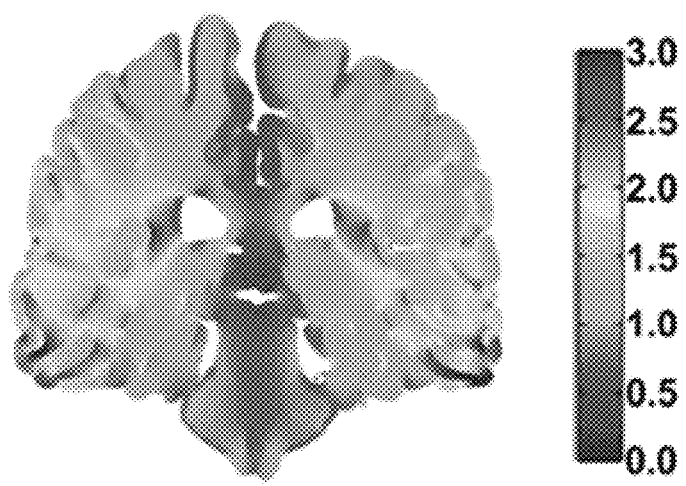
FIG. 7 illustrates electrical field magnitude and distribution (in V/cm) shown in coronal view from a finite element method simulation model.

In order to properly optimize array placement on a portion of a patient's body, the imaging data 610, such as MRI imaging data, may be analyzed by the patient modeling application 608 to identify a region of interest that comprises a tumor. In the context of a patient's head, to characterize how electrical fields behave and distribute within the human head, modeling frameworks based on anatomical head models using Finite Element Method (FEM) simulations may be used. These simulations yield realistic head models based on magnetic resonance imaging (MRI) measurements and compartmentalize tissue types such as skull, white matter, gray matter, and cerebrospinal fluid (CSF) within the head. Each tissue type may be assigned dielectric properties for relative conductivity and permittivity, and simulations may be run whereby different transducer array configurations are applied to the surface of the model in order to understand how an externally applied electrical field, of preset frequency, will distribute throughout any portion of a patient's body, for example, the brain. The results of these simulations, employing paired array configurations, a constant current, and a preset frequency of 200 kHz, have demonstrated that electrical field distributions are relatively non-uniform throughout the brain and that electrical field intensities exceeding 1 V/cm are generated in most tissue compartments except CSF. These results are obtained assuming total currents with a peak-to-peak value of 1800 milliamperes (mA) at the transducer array-scalp interface. This threshold of electrical field intensity is sufficient to arrest cellular proliferation in glioblastoma cell lines. Additionally, by manipulating the configuration of paired transducer arrays, it is possible to achieve an almost tripling of electrical field intensity to a particular region of the brain as shown in FIG. 7. FIG. 7 illustrates electrical field magnitude and distribution (in V/cm) shown in coronal view from a finite element method simulation model. This simulation employs a left-right paired transducer array configuration.

Figure 8A:
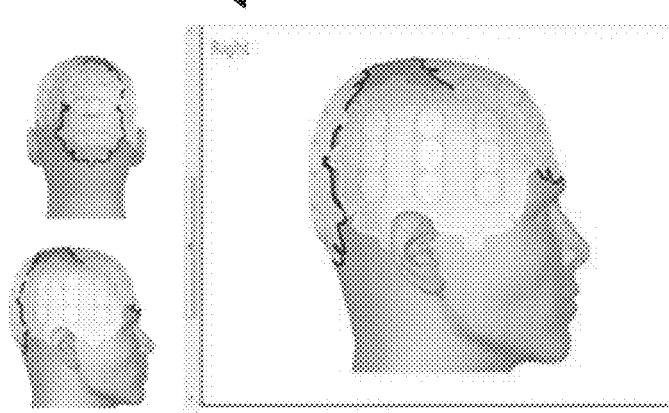
FIG. 8A shows a three-dimensional array layout map 800.
Figure 8B:
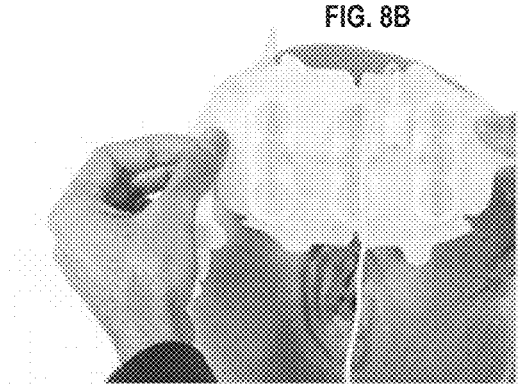
FIG. 8B shows placement of transducer arrays on the scalp of a patient.

In an aspect, the patient modeling application 608 may be configured to determine a desired (e.g., optimal) transducer array layout for a patient based on the location and extent of the tumor. For example, initial morphometric head size measurements may be determined from the T1 sequences of a brain MRI, using axial and coronal views. Postcontrast axial and coronal MRI slices may be selected to demonstrate the maximal diameter of enhancing lesions. Employing measures of head size and distances from predetermined fiducial markers to tumor margins, varying permutations and combinations of paired array layouts may be assessed in order to generate the configuration which delivers maximal electrical field intensity to the tumor site. As shown in FIG. 8A, the output may be a three-dimensional array layout map 800. The three-dimensional array layout map 800 (e.g., a transducer array layout map) may be used by the patient and/or caregiver in arranging arrays on the scalp during the normal course of TTFields therapy as shown in FIG. 8B.

In an aspect, the patient modeling application 608 can be configured to determine the three-dimensional array layout map for a patient. MRI measurements of the portion of the patient that is to receive the transducer arrays may be determined. By way of example, the MRI measurements may be received via a standard Digital Imaging and Communications in Medicine (DICOM) viewer. MRI measurement determination may be performed automatically, for example by way of artificial intelligence techniques or may be performed manually, for example by way of a physician.

Figure 9A:
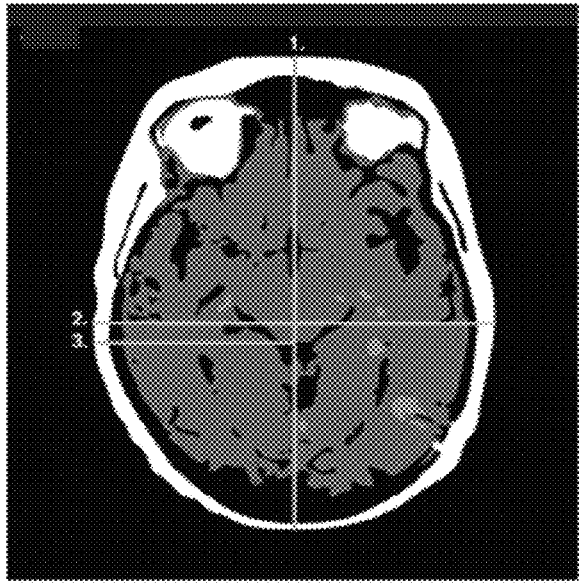
FIG. 9A shows an axial T1 sequence slice containing most apical image, including orbits used to measure head size.
Figure 9B:
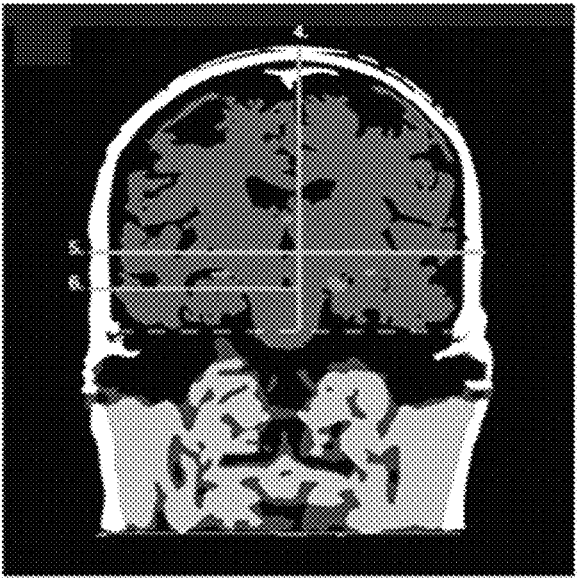
FIG. 9B shows a coronal T1 sequence slice selecting image at level of ear canal used to measure head size.
Figure 9C:
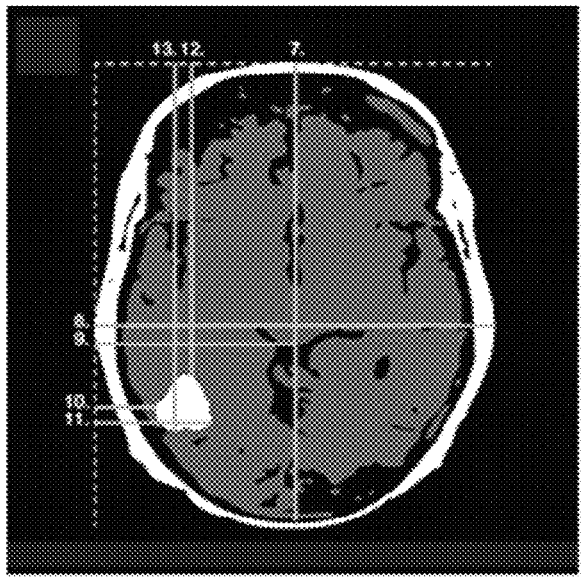
FIG. 9C shows a postcontrast T1 axial image shows maximal enhancing tumor diameter used to measure tumor location.
Figure 9D:
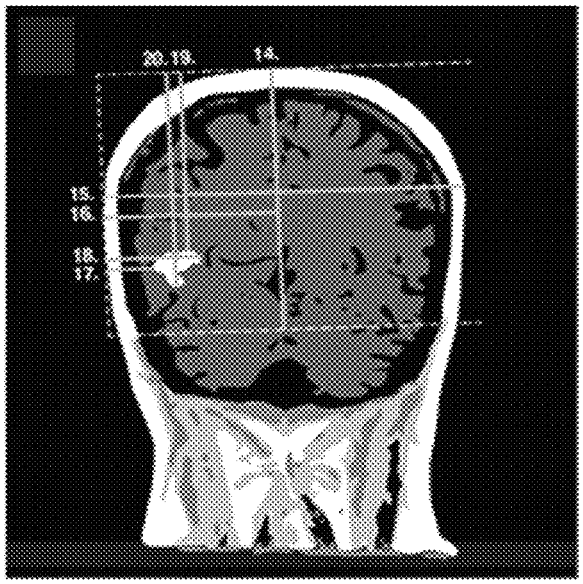
FIG. 9D shows a postcontrast T1 coronal image shows maximal enhancing tumor diameter used to measure tumor location.

Manual MRI measurement determination may comprise receiving and/or providing MRI data via a DICOM viewer. The MRI data may comprise scans of the portion of the patient that contains a tumor. By way of example, in the context of the head of a patient, the MRI data may comprise scans of the head that comprise one or more of a right fronto-temporal tumor, a right parieto-temporal tumor, a left fronto-temporal tumor, a left parieto-occipital tumor, and/or a multi-focal midline tumor. FIG. 9A, FIG. 9B, FIG. 9C, and FIG. 9D show example MRI data showing scans of the head of a patient. FIG. 9A shows an axial T1 sequence slice containing most apical image, including orbits used to measure head size. FIG. 9B shows a coronal T1 sequence slice selecting image at level of ear canal used to measure head size. FIG. 9C shows a postcontrast T1 axial image shows maximal enhancing tumor diameter used to measure tumor location. FIG. 9D shows a postcontrast T1 coronal image shows maximal enhancing tumor diameter used to measure tumor location. MRI measurements may commence from fiducial markers at the outer margin of the scalp and extend tangentially from a right-, anterior-, superior origin. Morphometric head size may be estimated from the axial T1 MRI sequence selecting the most apical image which still included the orbits (or the image directly above the superior edge of the orbits)

In an aspect, the MRI measurements may comprise, for example, one or more of, head size measurements and/or tumor measurements. In an aspect, one or more MRI measurements may be rounded to the nearest millimeter and may be provided to a transducer array placement module (e.g., software) for analysis. The MRI measurements may then be used to generate the three-dimensional array layout map (e.g., three-dimensional array layout map 800).

The MRI measurements may comprise one or more head size measurements such as: a maximal antero-posterior (A-P) head size, commencing measurement from the outer margin of the scalp; a maximal width of the head perpendicular to the A-P measurement: right to left lateral distance; and/or a distance from the far most right margin of the scalp to the anatomical midline.

The MRI measurements may comprise one or more head size measurements such as coronal view head size measurements. Coronal view head size measurements may be obtained on the T1 MRI sequence selecting the image at the level of the ear canal (FIG. 9B). The coronal view head size measurements may comprise one or more of: a vertical measurement from the apex of the scalp to an orthogonal line delineating the inferior margin of the temporal lobes; a maximal right to left lateral head width; and/or a distance from the far right margin of the scalp to the anatomical midline.

The MRI measurements may comprise one or more tumor measurements, such as tumor location measurements. The tumor location measurements may be made using T1 post-contrast MRI sequences, firstly on the axial image demonstrating maximal enhancing tumor diameter (FIG. 9C). The tumor location measurements may comprise one or more of: a maximal A-P head size, excluding the nose; a maximal right to left lateral diameter, measured perpendicular to the A-P distance; a distance from the right margin of the scalp to the anatomical midline; a distance from the right margin of the scalp to the closest tumor margin, measured parallel to the right-left lateral distance and perpendicular to the A-P measurement; a distance from the right margin of the scalp to the farthest tumor margin, measured parallel to the right-left lateral distance, perpendicular to the A-P measurement; a distance from the front of the head, measured parallel to the A-P measurement, to the closest tumor margin; and/or a distance from the front of the head, measured parallel to the A-P measurement, to the farthest tumor margin.

The one or more tumor measurements may comprise coronal view tumor measurements. The coronal view tumor measurements may comprise identifying the postcontrast T1 MRI slice featuring the maximal diameter of tumor enhancement (FIG. 9D). The coronal view tumor measurements may comprise one or more of: a maximal distance from the apex of the scalp to the inferior margin of the cerebrum. In anterior slices, this would be demarcated by a horizontal line drawn at the inferior margin of the frontal or temporal lobes, and posteriorly, it would extend to the lowest level of visible tentorium; a maximal right to left lateral head width; a distance from the right margin of the scalp to the anatomical midline; a distance from the right margin of the scalp to the closest tumor margin, measured parallel to the right-left lateral distance; a distance from the right margin of the scalp to the farthest tumor margin, measured parallel to the right-left lateral distance; a distance from the apex of the head to the closest tumor margin, measured parallel to the superior apex to inferior cerebrum line; and/or a distance from the apex of the head to the farthest tumor margin, measured parallel to the superior apex to inferior cerebrum line.

Other MRI measurements may be used, particularly when the tumor is present in another portion of the patient's body.

The MRI measurements may be used by the patient modeling application 608 to generate a patient model. The patient model may then be used to determine the three-dimensional array layout map (e.g., three-dimensional array layout map 800). Continuing the example of a tumor within the head of a patient, a healthy head model may be generated which serves as a deformable template from which patient models can be created. When creating a patient model, the tumor may be segmented from the patient's MRI data (e.g., the one or more MRI measurements). Segmenting the MRI data identifies the tissue type in each voxel, and electric properties may be assigned to each tissue type based on empirical data. Table 1 shows standard electrical properties of tissues that may be used in simulations. The region of the tumor in the patient MRI data may be masked, and non-rigid registration algorithms may be used to register the remaining regions of the patient head on to a 3D discrete image representing the deformable template of the healthy head model. This process yields a non-rigid transformation that maps the healthy portion of the patient's head in to the template space, as well as the inverse transformation that maps the template in to the patient space. The inverse transformation is applied to the 3D deformable template to yield an approximation of the patient head in the absence of a tumor. Finally, the tumor (referred to as a region-of-interest (ROI)) is planted back into the deformed template to yield the full patient model. The patient model may be a digital representation in three dimensional space of the portion of the patient's body, including internal structures, such as tissues, organs, tumors, etc.

TABLE 1

| Tissue Type | Conductivity, S/m | Relative Permittivity |
| --- | --- | --- |
| Scalp | 0.3 | 5000 |
| Skull | 0.08 | 200 |
| Cerebrospinal fluid | 1.79 | 110 |
| Gray matter | 0.25 | 3000 |
| White matter | 0.12 | 2000 |
| Enhancing tumor | 0.24 | 2000 |
| Enhancing nontumor | 0.36 | 1170 |
| Resection cavity | 1.79 | 110 |
| Necrotic tumor | 1 | 110 |
| Hematoma | 0.3 | 2000 |
| Ischemia | 0.18 | 2500 |
| Atrophy | 1 | 110 |
| Air | 0 | 0 |

Delivery of TTFields may then be simulated by the patient modeling application 608 using the patient model. Simulated electrical field distributions, dosimetry, and simulation-based analysis are described in U.S. Patent Publication No. 20190117956 A1 and Publication "Correlation of Tumor treating Fields Dosimetry to Survival Outcomes in Newly Diagnosed Glioblastoma: A Large-Scale Numerical Simulation-based Analysis of Data from the Phase 3 EF-14 randomized Trial" by Ballo, et al. (2019) which are incorporated herein by reference in their entirety.

To ensure systematic positioning of the transducer arrays relative to the tumor location, a reference coordinate system may be defined. For example, a transversal plane may initially be defined by conventional LR and anteroposterior (AP) positioning of the transducer arrays. The left-right direction may be defined as the x-axis, the AP direction may be defined as the y-axis, and the cranio-caudal direction normal to the xy-plane may be defined as the z-axis.

After defining the coordinate system, transducer arrays may be virtually placed on the patient model with their centers and longitudinal axes in the xy-plane. A pair of transducer arrays may be systematically rotated around the z-axis of the head model, i.e. in the xy-plane, from 0 to 180 degrees, thereby covering the entire circumference of the head (by symmetry). The rotation interval may be, for example, 15 degrees, corresponding to approximately 2 cm translations, giving a total of twelve different positions in the range of 180 degrees. Other rotation intervals are contemplated. Electrical field distribution calculations may be performed for each transducer array position relative to tumor coordinates.

Electrical field distribution in the patient model may be determined by the patient modeling application 608 using a finite element (FE) approximation of electrical potential. In general, the quantities defining a time-varying electromagnetic field are given by the complex Maxwell equations. However, in biological tissues and at the low to intermediate frequency of TTFields (f=200 kHz), the electromagnetic wavelength is much larger than the size of the head and the electric permittivity c is negligible compared to the real-valued electric conductivity σ, i.e., where $\omega=2\pi f$ is the angular frequency. This implies that the electromagnetic propagation effects and capacitive effects in the tissue are negligible, so the scalar electric potential may be well approximated by the static Laplace equation $\nabla \cdot (\sigma \nabla \phi)=0$, with appropriate boundary conditions at the electrodes and skin. Thus, the complex impedance is treated as resistive (i.e. reactance is negligible) and currents flowing within the volume conductor are, therefore, mainly free (Ohmic) currents. The FE approximation of Laplace's equation may be calculated using software, such as SimNIBS software (simnibs.org). Computations based on the Galerkin method and the residuals for the conjugate gradient solver are required to be <1E-9. Dirichlet boundary conditions were used with the electric potential was set to (arbitrarily chosen) fixed values at each set of electrode arrays. The electric (vector) field may be calculated as the numerical gradient of the electric potential and the current density (vector field) may be computed from the electrical field using Ohm's law. The potential difference of the electrical field values and the current densities may be linearly rescaled to ensure a total peak-to-peak amplitude for each array pair of 1.8 A, calculated as the (numerical) surface integral of the normal current density components over all triangular surface elements on the active electrode discs. The "dose" of TTFields may calculated as the intensity (L2 norm) of the field vectors. The modeled current may be assumed to be provided by two separate and sequentially active sources each connected to a pair of 3×3 transducer arrays. The left and posterior arrays may be defined to be sources in the simulations, while the right and anterior arrays were the corresponding sinks, respectively. However, as TTFields employ alternating fields, this choice is arbitrary and does not influence the results.

An average electrical field strength generated by transducer arrays placed at multiple locations on the patient may be determined by the patient modeling application 608 for one or more tissue types. In an aspect, the transducer array position that corresponds to the highest average electrical field strength in the tumor tissue type(s) may be selected as a desired (e.g., optimal) transducer array position for the patient.

In some instances, transducer array placement positions, such as optimized transducer array placement positions, may be determined for effective and/or optimized TTFields treatment and/or therapy. For example, one or more users (e.g., a physicians, nurses, assistants, staff members, physicists, dosimetrists, etc.) may use a user interface to determine and/or generate transducer array layout maps (e.g., three-dimensional array layout maps, etc.) for positioning transducer arrays on the body (e.g., head, torso, etc.) of a person (e.g., patient, subject, etc.) that will optimize TTFields treatment and/or therapy while avoiding and/or limiting skin toxicity. For example, a plurality of sets (e.g., groups, compendiums, etc.) of transducer array layout maps may be determined that each include transducer array layout maps that satisfy criteria or a criterion. A criterion may include a potential magnitude of an electric field distributed within a region-of-interest (ROI) associated with a person (e.g., patient, subject, etc.), a potential power density associated with an electric field distributed within the ROI, and an estimate of skin toxicity associated with a portion of the body (e.g., head, torso, etc.) of the person, and/or any other criterion. Sets of transducer array layout maps of the plurality of sets of transducer array layout maps may be determined that include two or more transducer array layout maps that include non-overlapping positions for transducer array placement. The plurality of sets of transducer array layout maps may be displayed, for example, to a user, and/or be selectable, for example, via a user interface. The user interface may be used to select a transducer array layout map, and based on the selection, be presented with sets of transducer array layout maps of the plurality of sets of transducer array layout maps that are associated with (e.g., based on a criterion, based on non-overlapping positions, overlapping positions, etc.) the selected transducer array layout map.

An example method may include presenting a plurality of images of an anatomic volume to at least one user, and accepting, from the at least one user, a selection of which images of the anatomic volume should be used to generate a plurality of transducer array layout maps. The method may include generating a model (3D model) of electrical characteristics of the anatomic volume based on the selected images and determining a plurality of transducer array layouts. Then evaluating, based on the created model, which of the determined transducer array layouts satisfies at least one criterion. The method may include presenting, to the at least one user, a plurality of transducer array layout maps that satisfy the at least one criterion and accepting, from the at least one user, a selection of one of the transducer array layouts that was presented to the at least one user. A report that describes the selected transducer array layout may be generated. In some instances, the model may also be based on at least one additional image. In some instances generating the model may include performing segmentation based on input received from the at least one user. In some instances, the at least one user may include a first user and a second user. The method may also include accepting an input from the first user identifying a region of interest, and outputting data describing the region of interest to the second user. In some instances, generating the model may include performing segmentation based on input received from the second user. In some instances, the method may include accepting an input from the first user identifying a gross segmentation, and outputting data describing the gross segmentation to the second user. In some instances, generating the model may include performing segmentation based on input received from the second user. In some instances, the method may include accepting at least one note from the first user, and outputting the at least one note to the second user. In some instances, generating the model may include performing segmentation based on input received from the second user. In some instances, the method may include accepting an input from the first user identifying an avoidance region, and outputting data describing the avoidance region to the second user. In some instances, generating the model may include performing segmentation based on input received from the second user.

Figure 10:
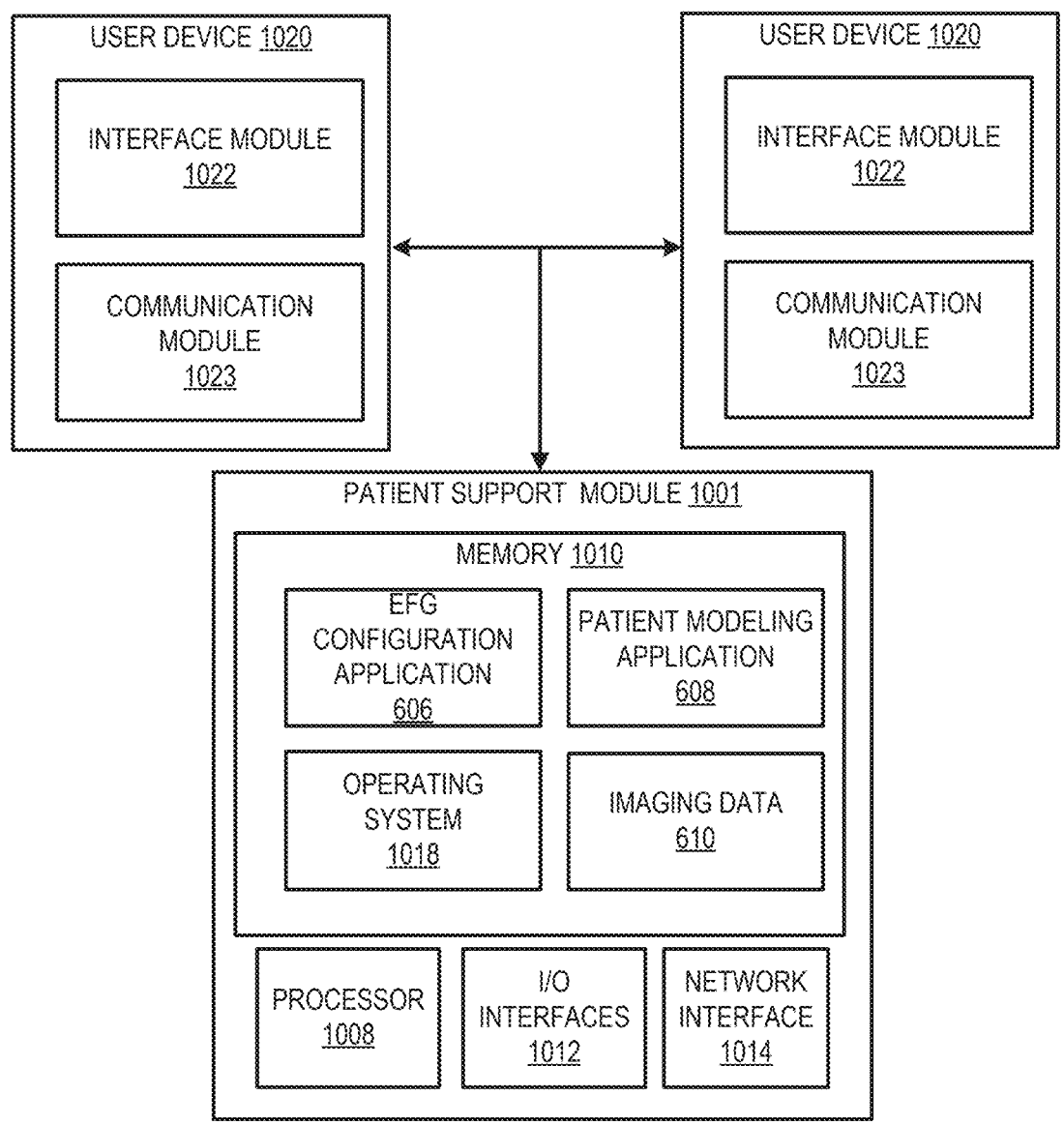
FIG. 10 shows an example system for managing transducer array placement.

FIG. 10 is a block diagram depicting an example system 1000 for managing transducer array placement. In some instances, components of the system 1000 may be implemented as a single device and/or the like. In some instances, components of the system 1000 may be implemented as separate devices/components and/or in collective communication. The system 1000 and/or the components of the system 1000 may be implemented as hardware, software, or a combination of both hardware and software. In an aspect, some or all steps of any described method herein may be performed on and/or via components of the system 1000. The system 1000 may be used to determine positions (locations) for transducer array placement on the body of a person (e.g., a patient, a subject, etc.). The positions (locations) for transducer array placement may be indicated by one or more transducer array layout maps. A user (e.g., a physician, a nurse, an assistant, a staff member, a physicist, a dosimetrist, etc.) may use the system 1000 to generate and/or evaluate a plurality of transducer array layout maps. The system 1000 enables users that may be higher-cost and/or highly skilled personnel (e.g., physicians, etc.) to provide guidance and/or instructions for determining and/or generating transducer array layout maps to lower-cost personnel (e.g., dosimetrists, physicists, etc.). For example, image data (e.g., one or more images associated with CT, MRI, ultrasound, SPECT, x-ray CT, PET, etc.), may be segmented via a user device and the segmented image data may be sent to another user device for analysis, used to generate a three-dimensional (3D) model, and/or used to generate a plurality of transducer array layout maps. Determined and/or generated transducer array layout maps may be reviewed and/or selected to generate a report that may be used for effective TTFields treatment and/or therapy.

The system 1000 may include a patient support module 1001. The patient support module 1001 may include a processor 1008. The processor 1008 may be a hardware device for executing software, particularly that stored in memory 1010. The processor 1008 may be any custom made or commercially available processor, a central processing unit (CPU), an auxiliary processor among several processors associated with the patient support module 1001, a semiconductor-based microprocessor (in the form of a microchip or chip set), or generally any device for executing software instructions. When the patient support module 1001 is in operation, the processor 1008 may be configured to execute software stored within the memory 1010, to communicate data to and from the memory 1010, and to generally control operations of the patient support module 1001 pursuant to the software.

The I/O interfaces 1012 may be used to receive user input from and/or for providing system output to one or more devices or components, such as user devices 1020 and 1030. User input may be provided via, for example, a keyboard, mouse, a data/information communication interface, and/or the like. The I/O interfaces 1012 may include, for example, a serial port, a parallel port, a Small Computer System Interface (SCSI), an IR interface, an RF interface, and/or a universal serial bus (USB) interface.

A network interface 1014 may be used to transmit and receive data/information from the patient support module 1001. The network interface 1014 may include, for example, a 10BaseT Ethernet Adaptor, a 100BaseT Ethernet Adaptor, a LAN PHY Ethernet Adaptor, a Token Ring Adaptor, a wireless network adapter (e.g., WiFi), or any other suitable network interface device. The network interface 1014 may include address, control, and/or data connections to enable appropriate communications.

The memory 1010 (memory system) may include any one or combination of volatile memory elements (e.g., random access memory (RAM, such as DRAM, SRAM, SDRAM, etc.)) and nonvolatile memory elements (e.g., ROM, hard drive, tape, CDROM, DVDROM, etc.). Moreover, the memory 1010 may incorporate electronic, magnetic, optical, and/or other types of storage media. In some instances, the memory system 1010 may have a distributed architecture, where various components are situated remote from one another, but may be accessed by the processor 1008.

The memory 1010 may include one or more software programs, each of which comprises an ordered listing of executable instructions for implementing logical functions. For example the memory 1010 may include the EFG configuration application 606, the patient modeling application 608, the imaging data 610, as described in FIG. 6, and a suitable operating system (O/S) 1018. The operating system 1018 may, essentially, control the execution of other computer programs, and provides scheduling, input-output control, file and data management, memory management, and communication control and related services.

For purposes of illustration, application programs and other executable program components such as the operating system 1018 are illustrated herein as discrete blocks, although it is recognized that such programs and components can reside at various times in different storage components of the patient support system 104. An implementation of the EFG configuration application 606, the patient modeling application 608, the imaging data 610, and/or the control software 110 can be stored on or transmitted across some form of computer readable media. Any of the disclosed methods can be performed by computer readable instructions embodied on computer readable media. Computer readable media can be any available media that can be accessed by a computer. By way of example and not meant to be limiting, computer readable media can comprise "computer storage media" and "communications media." "Computer storage media" can comprise volatile and nonvolatile, removable and non-removable media implemented in any methods or technology for storage of information such as computer readable instructions, data structures, program modules, or other data. Exemplary computer storage media can comprise RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by a computer.

The system 1000 may include the user devices 1020 and 1030. The user devices 1020 and 1030 may be an electronic devices such as computers, smartphones, laptops, tablets, and/or the like capable of communicating with a patient support module 1001. Although only the user devices 1020 and 1030, the system 1000 may include a plurality of the devices.

The user devices 1020 and 1030 may include an interface module 1022. The interface module 1022 may provide an interface for users to interact with the user devices 1020 and 1030 and/or the patient support module 1001. The interface module 1022 may include one or more input devices/interfaces such as a keyboard, a pointing device (e.g., a computer mouse, remote control), a microphone, a joystick, a scanner, haptic sensing and/or tactile input devices, and/or the like.

The interface module 1022 may include one or more interfaces for presenting and/or receiving information to/from a user (e.g., a physician, a nurse, an assistant, a staff member, a physicist, a dosimetrist, etc.), such as user feedback. The interface module 1022 may include any software, hardware, and/or interfaces used to provide communication between users and one or more of the user devices 1020 and 1030, the patient support module 1001, and/or any other component of and/or associated with the system 1000. The interface module 1022 may include one or more displays (e.g., monitors, head-up displays, head mounted displays, liquid crystal displays, organic light-emitting diode displays, active-matrix organic light-emitting diode displays, stereo displays, etc.) for displaying/presenting information to the user. The interface module 1022 may include one or more audio device (e.g., stereos, speakers, microphones, etc.) for capturing/obtaining audio information and conveying audio information, such as audio information captured/obtained from the user and/or conveyed to the user. The interface module 1022 may include a graphical user interface (GUI), a web browser (e.g., Internet Explorer®, Mozilla Firefox®, Google Chrome®, Safari®, or the like), an application/API. The interface module 1022 may request and/or query various files from a local source and/or a remote source, such as the patient support module 1001.

The interface module 1022 may transmit/send data/information to a local and/or remote device/component of the system 1000 such as the patient support module 1001 and/or another user device (e.g., the user device 1020, the user device 1030, etc.). The user devices 1020 and 1030 may include a communication module 1023. The communication module 1023 may enable the user devices 1020 and 1030 to communicate with components of the system 1000, such as the patient support module 1001 and/or another user device, via wired and/or wireless communication techniques. For example, the communication module 1023 may utilize any suitable wired communication technique, such as Ethernet, coaxial cable, fiber optics, and/or the like. The communication module 1023 may utilize any suitable long-range communication technique, such as Wi-Fi (IEEE 802.11), BLUETOOTH®, cellular, satellite, infrared, and/or the like. The communication module 1023 may utilize any suitable short-range communication technique, such as BLUETOOTH®, near-field communication, infrared, and the like.

As described, the system 1000 may be used to determine positions (locations) for transducer array placement on the body of a person (e.g., a patient, a subject, etc.). The positions (locations) for transducer array placement may be indicated by one or more transducer array layout maps. A user (e.g., a physician, a nurse, an assistant, a staff member, a physicist, a dosimetrist, etc.) may use the system 1000 generate and/or evaluate a plurality of transducer array layout maps. The system 1000 enables users that may be higher-cost and/or highly skilled personnel (e.g., physicians, etc.) to provide guidance and/or instructions for determining and/or generating transducer array layout maps to lower-cost personnel (e.g., dosimetrists, physicists, etc.). For example, the higher-cost and/or highly skilled personnel may use the user device 1020 to provide guidance and/or instructions for determining and/or generating transducer array layout maps to the lower-cost personnel (e.g., dosimetrists, physicists, etc.) who may be a user of the user device 1030.

Figure 11A:
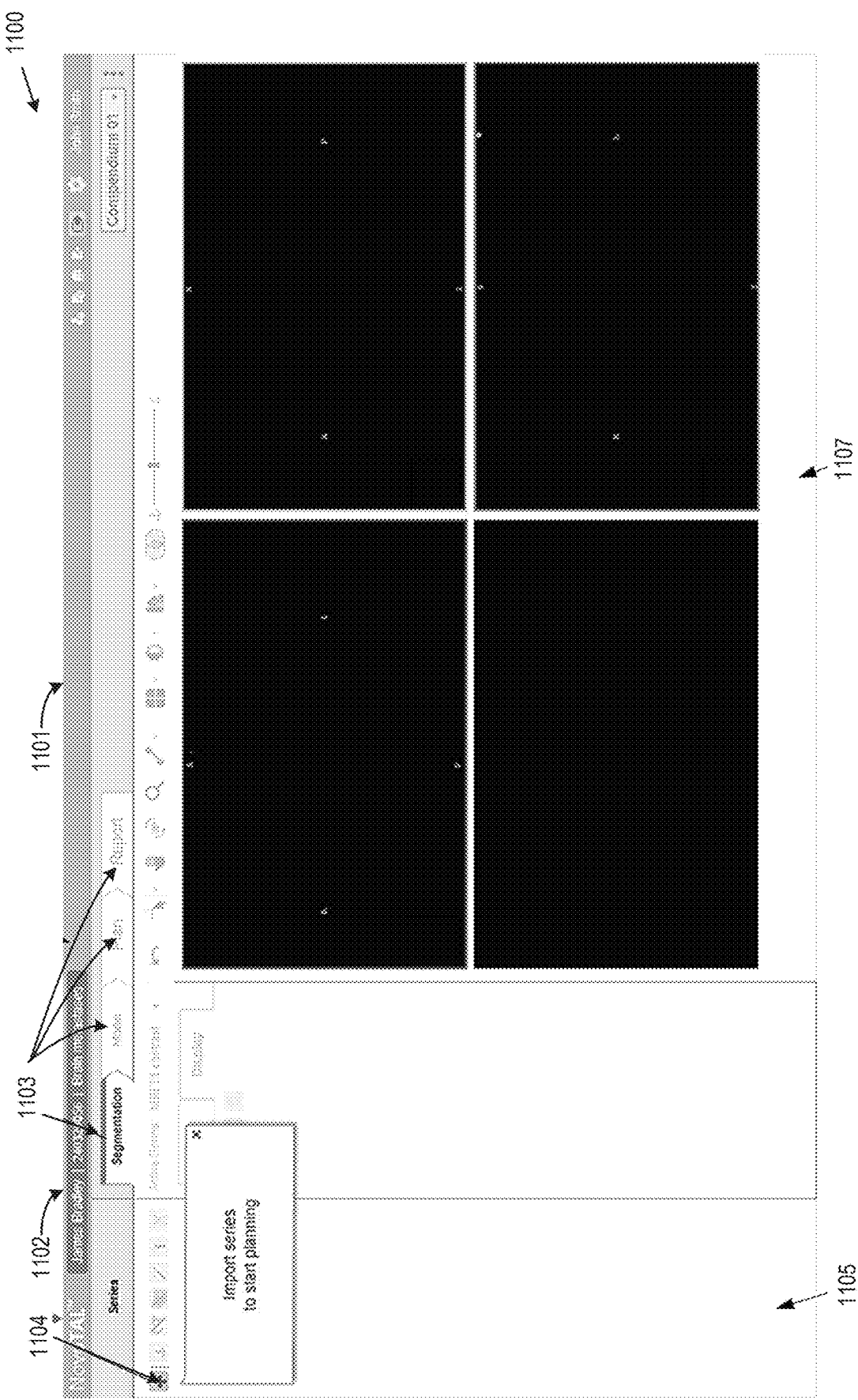
FIGS. 11A-11D shows an example user interface for managing transducer array placement.

FIGS. 11A-11D show screens of an example interface (e.g., the interface module 1022, etc.) for managing transducer array placement. One or more images of a portion of the body (e.g., a head, a torso, an anatomic volume, etc.) of a subject/patient, for example from the image data 610, may be segmented and used to generate a three-dimensional (3D) model. FIG. 11A shows an example screen 1101 of a user interface 1100. The screen 1101 may include subject/patient identifying information 1102. The identifying information 1102 may identify a subject/patient associated with one or more images used to generate a 3D model. Progression through the user interface 1100 may be enabled and/or indicated by interactive elements 1103 (e.g., tabs, etc.). As indicted by the interactive element 1103, the screen 1101 may be used for segmentation of image data.

Figure 11B:
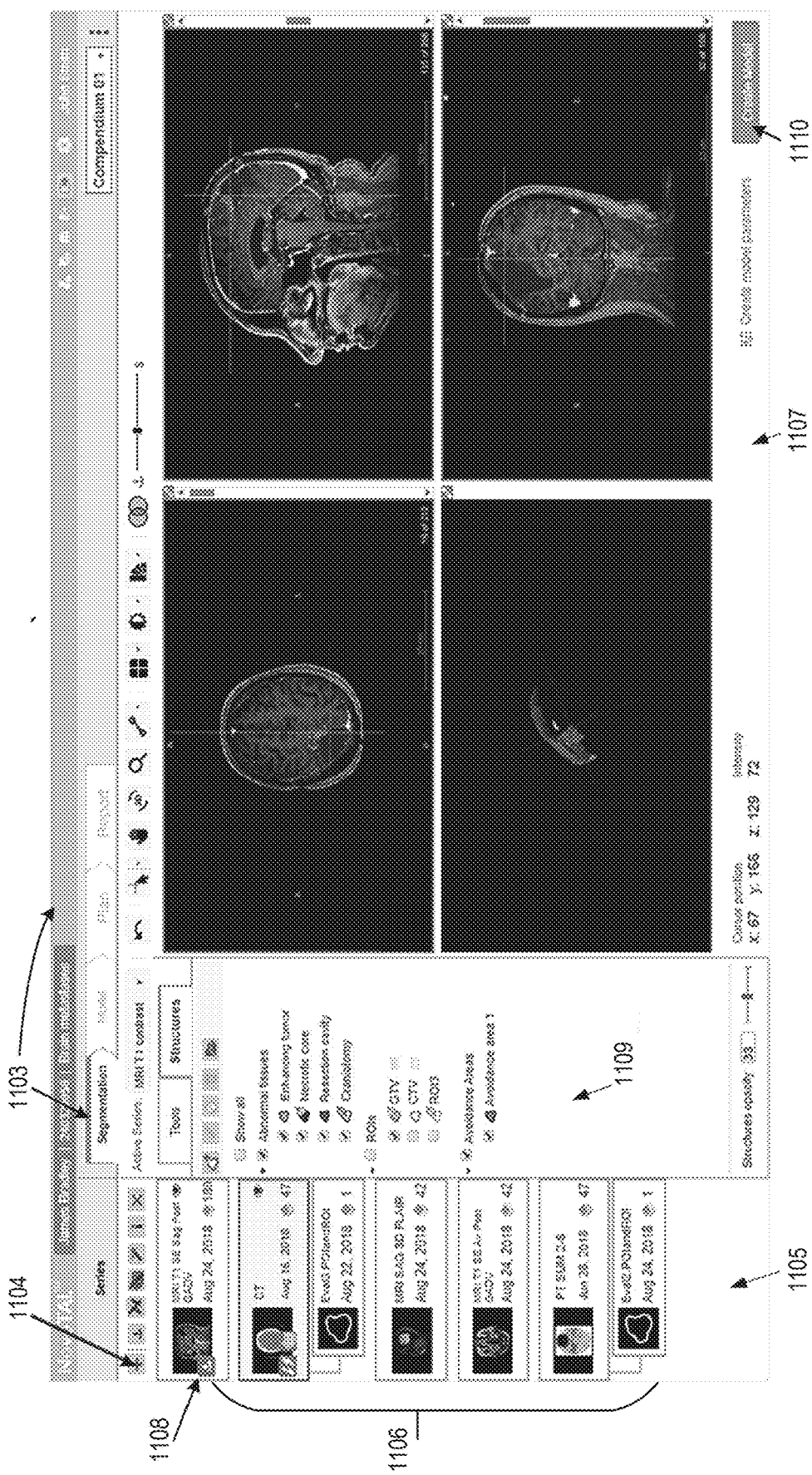

The screen 1101 enables a user (e.g., a user of the user devices 1020 and 1030, etc.) to import and inspect one or more images of a portion of the body (e.g., a head, a torso, an anatomic volume, etc.) of a subject/patient and determine if the imaged should be used to generate a 3D model. The images may be imported, for example, from the patient support module 1001, by interacting with an interactive element 1104 (e.g., button, etc.). Interacting with an interactive element 1104 may cause a menu that enables the user to search for relevant images and/or upload the relevant images to open. After an image has been imported, from example, from the image data 610, a representation of the images may be shown in a panel 1105. FIG. 11B shows the example screen 1101 of the user interface 1100 when images have been imported and are represented in the panel 1105 by the images 1106. The user can view and inspect the imported images 1106, for example, by using an interactive element (e.g., mouse, touch pad, etc.) to drag one or more of the images 1106 to one or more windows 1107 of the screen 1101. The user may identify images (e.g., one or more images, sets of images, etc.) best suited for TTFields treatment planning. As shown in FIG. 11B, one or more of the images 1106 are represented in the windows 1107.

After viewing/inspecting the images 1106 the user may select an image or sets of images to be segmented and used to generate a 3D model. In some instances, a user of the user device 1020 may select an image or sets of images, and the user device 1020 may send the selected image or sets of images (e.g., information associated with the selected image or sets of images, etc.) to the user device 1030 for segmentation and 3D model generation. In some instances, a user of the user device 1030 may select an image or sets of images, and the user device 1030 may send the selected image or sets of images (e.g., information associated with the selected image or sets of images, etc.) to the user device 1020 for segmentation and 3D model generation. When selecting an image or sets of images, an image may be marked with an element 1108, such as an "anchor" icon that indicates that the image is a primary ("anchor") image that will be used to generate the computational 3D model and/or transducer array layout map. Other images may be marked as "assisting images" to indicate that the user has optionally selected the images to assist in generating the 3D model and/or transducer array layout map. The assisting images may be registered to the primary image to improve the accuracy of the 3D model. In some instances, the quality of a 3D model and/or transducer array layout map may be proportional to the number of images used to generate the 3D model and/or transducer array layout map.

The user may select images represented in the one or more windows 1107. After images have been selected, the images may be segmented to identify/determine/select features of and/or regions-of-interest within the images, such as represented tumor and/or abnormal tissue structures. The user interface 1100 may be configured with segmentation tools (e.g., semi-automatic segmentation tool, manual segmentation tools, etc.) and/or algorithms that enable the user to mark features, structures, and/or regions-of-interest (RO1) within the images. For example, the segmentation tools may enable the user to mark areas of images as an enhancing tumor, a necrotic core, a resection cavity, craniotomy, and/or the like. The area 1109 of the screen 1101 shows examples of structures in images that may be defined by a user, such as tissue types, ROIs, and avoidance structures/areas. An avoidance structure/area may be any region on the surface of the body of a subject/patient where a transducer arrays should not be placed, such as an area of scar tissue, medical apparatus implantation, and/or the like.

As described, a user may assign tissue types to images used to generate a 3D model and/or transducer array layout map. When a user assigns a tissue type to a specific voxel of an image, a corresponding voxel in a 3D model is assigned the same tissue type dielectric and/or electric properties associated with the tissue type. Each ROI determined and/or selected by a user may be assigned a unique label. The user interface 1100 enables any determined and/or selected ROI to be optionally marked on images used to generate a 3D model and/or transducer array layout map. In some instances, any determined and/or selected ROI may be used by an electrical field distribution simulation and/or optimization algorithm to generate transducer array layout maps. In some instances, ROIs may be imported to the system 1000 from an outside source (e.g., a third-party software used for planning radiation therapy, etc.). After a user completes segmentation edits to images, an interactive element 1110 may be interacted with and/or selected to generate a 3D model.

Figure 11C:
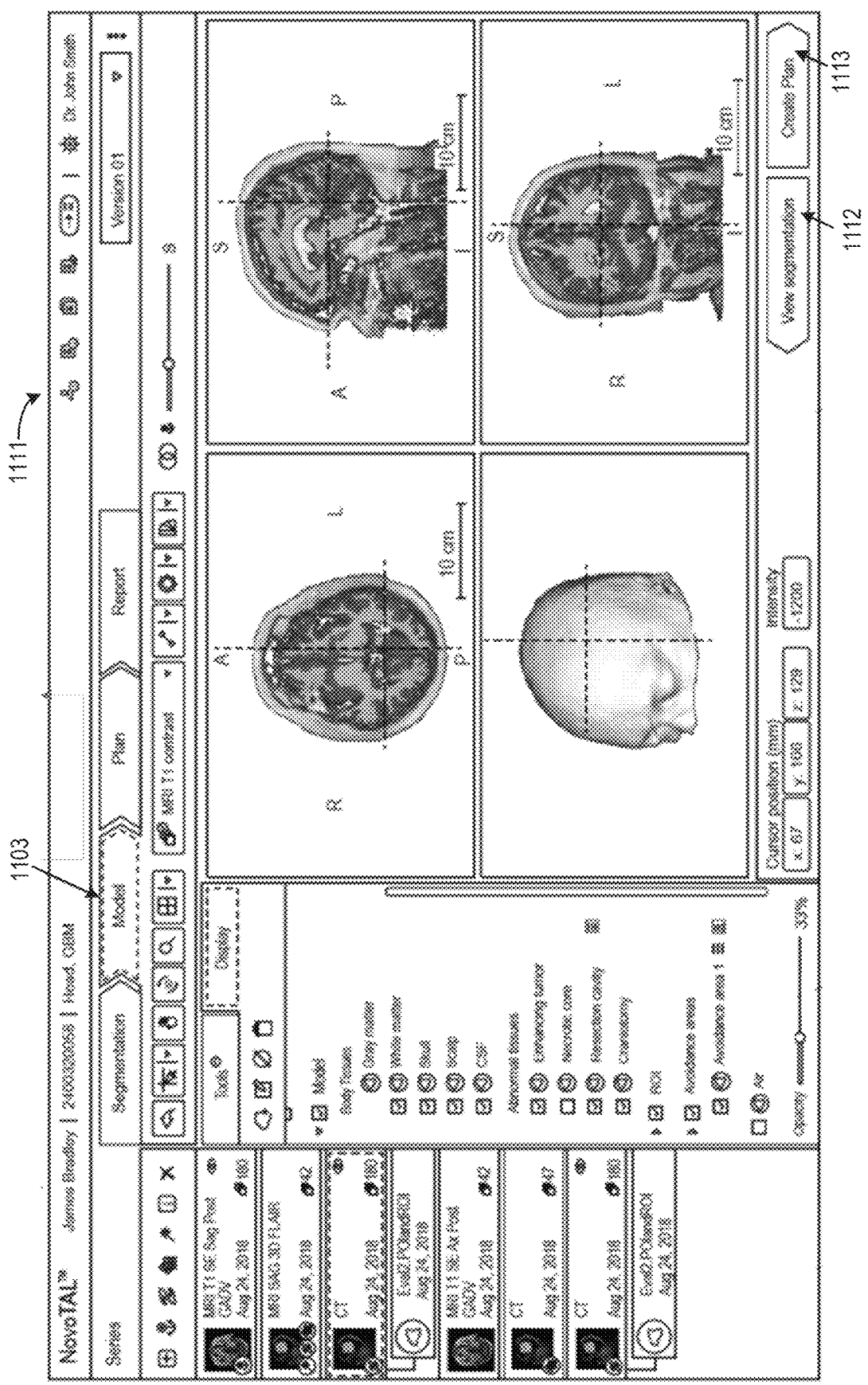

FIG. 11C shows an example screen 1111 of the user interface 1100. The screen 1111 may be a progression screen of the screen 1101. As shown, the interactive element 1103 is set to "model" to indicate the progression through of the user interface 1100. The screen 1111 may display any abnormal tissues indicated on the screen 1101 and any normal body tissues (e.g., gray matter, white matter, skull, scalp, and CSF) within images. The user interface 1100 may be configured to automatically add and/or include any normal body tissues when generating a 3D model.

A generated 3D model may model any electrical characteristics at every point in space within a portion of the body (e.g., a head, a torso, an anatomic volume, etc.) of a subject/patient. For example, the system 1000 may map electrical characteristics to 3D models. Mapping electrical characteristics to 3D models may be based on Diffusion Tensor Imaging MRI data (DTI), Water Electric Property Tomography (wEPT), machine learning, and/or any other method/technique for associating electrical characteristics to tissue types based on image data. Once a 3D model is generated, the user interface 1100 enables a user to positioning simulated transducer arrays at various positions (locations) on the 3D model, simulate the application of AC voltages to the simulated transducer arrays, execute simulations that determine a resulting electric field distribution and/or power density at every point within the portion of the body (e.g., a head, a torso, an anatomic volume, etc.) of a subject/patient represented by the 3D model. The 3D model may be displayed to a user. If the user is not satisfied with the displayed model, an interactive element 1112 "view segmentation," for example, may be used to return to a previous screen, such as a segmentation input screen of the user interface 1100. If the user is satisfied with the displayed model, an interactive element 1113 "create plan," for example, may be used to proceed to a next screen of the user interface 1100.

Figure 11D:
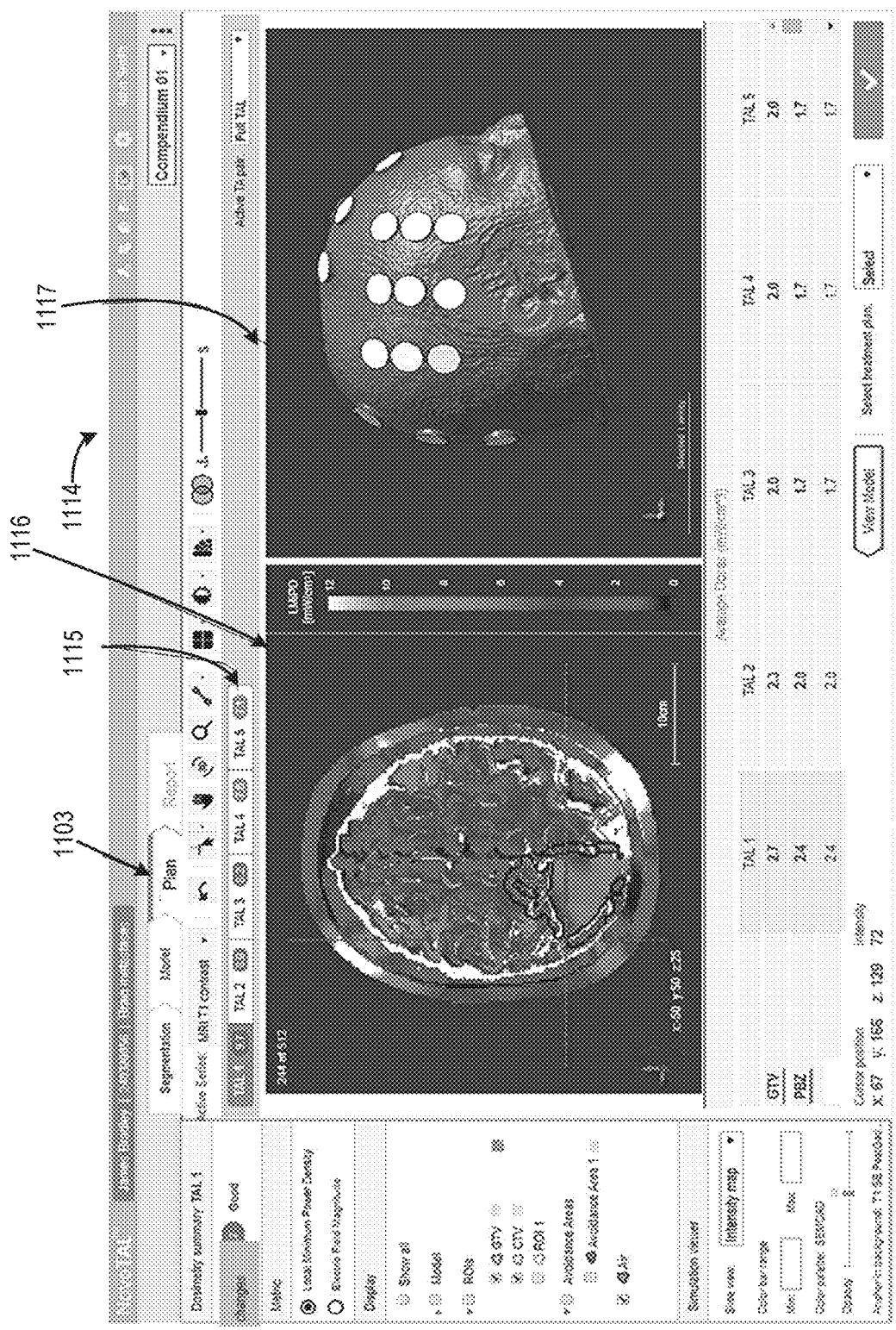

FIG. 11D shows an example screen 1114 of the user interface 1100. A user may interact with the interactive element 1103 "plan," for example to progress to the screen 1114. The screen 1114, for example, may be used analyze, evaluate, and/or select a TTfields treatment plan. For example, after a 3D is generated and a plurality of simulated electrical field distributions are determined based on the 3D model, a plurality of transducer array layout maps may be generated. In some instances, the system 1000 may determine the plurality of transducer array layouts, for example, from a library, record, corpus, and/or the like of standard transducer array layouts. In some instances, the system 1000 may determine the plurality of transducer array layouts, for example, enabling a user to use the user interface 1100 to varying the positions of one or more arrays to converge on a transducer array layout map that provides desired and/or the best (e.g., most suitable for satisfying a criterion, etc.) results. The system 1000, based on varying the positions of one or more arrays as described, may determine one or more transducer array layout maps (e.g., sets of transducer array layout mays, etc.) of a plurality of transducer array layout maps that optimizes electric field distribution within a target ROI while also satisfying constraints associated with transducer array placement imposed by avoidance structures. For example, one or more sets of transducer array layout maps may be determined (e.g., automatically, manually selected, etc.) from the plurality of transducer array layout maps that each represents at least two transducer array layout maps with non-overlapping positions and/or satisfy a criterion. As described, a criterion may include a magnitude of a simulated electric field distribution within a ROI associated with a 3D model, a power density associated with a simulated electric field distribution within the ROI, and/or the like. In some instances, a criterion may be based on an estimate of skin toxicity associated with a portion of the body of a subject/patient where transducer arrays are to be place and/or an avoidance area.

The best transducer array layout maps for a desired TTFields treatment plan may be determined to generate composite data (e.g., a report, a plan, a summary, etc.). The composite data, for example, may include information associated with the transducer array layout maps and associated simulated electrical field distributions. The composite data may be displayed, for example, via the user interface 1100. Returning to FIG. 11D, the screen 1114 may display electric field distributions (e.g., represented as one or more colormaps, etc.) associated with each transducer array layout map of the plurality of transducer array layout maps. For example, interactive elements 1115, may be used to view electric field distribution for each of the transducer array layout map (TALs) by interacting with a corresponding TAL element (e.g., TAL 1 through TAL 5). As shown, the TAL 1 of the interactive elements 1115 is selected and a colormap of the electric field distribution and the associated transducer array layout map are displayed in regions 1116 and 1117, respectively. A table summarizing the electric field dose delivered to target ROIs for each transducer array layout map of the plurality of transducer array layout maps may be displayed to enable a user to select a TTFields treatment plan. In some instances, an overall score for each transducer array layout map and/or set of transducer array layout maps of the plurality of transducer array layout maps may be determined and displayed. A score may represent a degree of satisfaction of a criterion or criteria by an associated transducer array layout map. Scores may be color-coded (e.g., green for the highest scores, yellow for intermediate scores, and red for low scores). The plurality of transducer array layout maps and/or sets of transducer array layout maps of the plurality of transducer array layout maps may ranked according to any method, algorithm, and/or criteria, and the ranking may be displayed to a user.

The user interface 1100 enables the plurality of transducer array layout maps and/or sets of transducer array layout maps to be evaluated, for example, by a user. An evaluation of a transducer array layout map be based on and/or determine a quality of a 3D model used to generate transducer array layout map (e.g., the TTFields treatment plan, etc.). A user may evaluate and select one or more transducer array layout maps and/or sets of transducer array layout maps of the plurality of transducer array layout maps.

FIG. 12, shows a flowchart of a method 1200 for managing transducer array placement. One or more of the apparatus 100, the patient support system 602, the patient modeling application 608, the system 1000, and/or any other device/component described herein can be configured to perform a method 1200 comprising, at 1210, generating a three-dimensional (3D) model of a portion of the subject's body. Generating the 3D model may be based on image data from any modality of imaging, such as one or more images associated with CT, MRI, ultrasound, SPECT, x-ray CT, PET, a combination thereof, and/or the like. In some instances, one or more user devices may display a plurality of images of the portion of the subject's body. A selection of one or more images of the plurality of images may be received based on a region-of-interest (ROI), and a 3D model may be generated based on the one or more images. For example, an ROI may be based on features and/or structures within the one or more images, such as an enhancing tumor, a necrotic core, a resection cavity, craniotomy, and/or the like. In some instances receiving information associated with the ROI may be received from a first user device of the one or more user devices, and a selection of the one or more images may be received from a second user device of the one or more user device.

At 1220, determining, based on the 3D model and a plurality of simulated electrical field distributions, a plurality of transducer array layout maps. Determining the plurality of transducer array layout maps may include determining, based on the 3D model, a plurality of pairs of positions for transducer array placement. In some instances, the plurality of pairs of positions for transducer array placement may be determined from a library, record, corpus, and/or the like of standard transducer array layouts. In some instances, the plurality of pairs of positions for transducer array placement may be determined and/or selected to avoid one or more regions within the 3D model (e.g., avoidance regions, etc.), and/or the like. For each pair of positions of the plurality of pairs positions, a simulated electrical field distribution of the plurality of simulated electrical field distributions may be determined. Determining the simulated electrical field distribution for each pair of positions of the plurality of pairs positions may include simulating, at a first position of the pair of positions, a first electrical field generated by a first transducer array, and simulating, at a second position of the pair of positions, a second electrical field generated by a second transducer array. The second position may be opposite the first position. In some instances, a third electrical field generated by the first transducer array may be simulated at a third position, and a fourth electrical field generated by the second transducer array may be simulated at a fourth position opposite the third position, and, based on the third electrical field and the fourth electrical field, the simulated electrical field distribution may be determined. The simulated electrical field distribution may be determined based on the first electrical field and the second electrical field and/or the third electrical field and the fourth electrical field. The plurality of transducer array layout maps may be determined based on the plurality of simulated electrical field distributions.

At 1230, determining, from the plurality of transducer array layout maps, one or more sets of transducer array layout maps, wherein each set of transducer array layout maps represents at least two transducer array layout maps with non-overlapping positions of a plurality of pairs of positions for transducer array placement, wherein the at least two transducer array layout maps satisfy a criterion. The criterion may include a magnitude of a simulated electric field distribution of the plurality of simulated electrical field distributions within a region-of-interest (ROI) associated with the 3D model, a power density associated with a simulated electric field distribution of the plurality of simulated electrical field distributions within the ROI, and an estimate of skin toxicity associated with the portion of the subject's body.

At 1240, causing display of the one or more sets of transducer array layout maps. The one or more sets of transducer array layout maps may be displayed by an interface of the one or more user devices. A selection of a set of transducer array layout maps of the one or more sets of transducer array layout maps may be received, for example via an interface of the one or more user devices. Composite data (e.g., a report, a plan, a summary, etc.) may be generated based on the selected set of transducer array layout maps. The composite data may include information associated with the selected set of transducer array layout maps and simulated electrical field distributions of the plurality of simulated electrical field distributions associated with the selected set of transducer array layout maps. The composite data may be sent to the one or more user devices.

FIG. 13, shows a flowchart of a method 1300 for managing transducer array placement. One or more of the apparatus 100, the patient support system 602, the patient modeling application 608, the system 1000, and/or any other device/component described herein can be configured to perform a method 1300 comprising, at 1310, generating a three-dimensional (3D) model of a portion of the subject's body. Generating the 3D model may be based on image data from any modality of imaging, such as one or more images associated with CT, MRI, ultrasound, SPECT, x-ray CT, PET, a combination thereof, and/or the like. In some instances, one or more user devices may display a plurality of images of the portion of the subject's body. A selection of one or more images of the plurality of images may be received based on a region-of-interest (ROI), and a 3D model may be generated based on the one or more images. For example, an ROI may be based on features and/or structures within the one or more images, such as an enhancing tumor, a necrotic core, a resection cavity, craniotomy, and/or the like. In some instances receiving information associated with the ROI may be received from a first user device of the one or more user devices, and a selection of the one or more images may be received from a second user device of the one or more user device.

At 1320, determining, based on the 3D model and a plurality of simulated electrical field distributions, a plurality of transducer array layout maps. Determining the plurality of transducer array layout maps may include determining, based on the 3D model, a plurality of pairs of positions for transducer array placement. In some instances, the plurality of pairs of positions for transducer array placement may be determined from a library, record, corpus, and/or the like of standard transducer array layouts. In some instances, the plurality of pairs of positions for transducer array placement may be determined and/or selected to avoid one or more regions within the 3D model (e.g., avoidance regions, etc.), and/or the like. For each pair of positions of the plurality of pairs positions, a simulated electrical field distribution of the plurality of simulated electrical field distributions may be determined. Determining the simulated electrical field distribution for each pair of positions of the plurality of pairs positions may include simulating, at a first position of the pair of positions, a first electrical field generated by a first transducer array, and simulating, at a second position of the pair of positions, a second electrical field generated by a second transducer array. The second position may be opposite the first position. In some instances, a third electrical field generated by the first transducer array may be simulated at a third position, and a fourth electrical field generated by the second transducer array may be simulated at a fourth position opposite the third position, and, based on the third electrical field and the fourth electrical field, the simulated electrical field distribution may be determined. The simulated electrical field distribution may be determined based on the first electrical field and the second electrical field and/or the third electrical field and the fourth electrical field. The plurality of transducer array layout maps may be determined based on the plurality of simulated electrical field distributions.

At 1330, receiving a selection of a first transducer array layout map of the plurality of transducer array layout maps, wherein the first transducer array layout map satisfies a criterion. The selection first transducer array layout may be received from one or more user devices. The criterion may include a magnitude of a simulated electric field distribution of the plurality of simulated electrical field distributions within a region-of-interest (ROI) associated with the 3D model, a power density associated with a simulated electric field distribution of the plurality of simulated electrical field distributions within the ROI, and an estimate of skin toxicity associated with the portion of the subject's body.

At 1340, determining, from the plurality of transducer array layout maps, one or more associated transducer array layout maps. Each associated transducer array layout map may include positions for transducer array placement that do not overlap positions for transducer array placement of the first transducer array layout map. In some instances, each associated transducer array layout map may satisfy the criterion.

At 1350, receiving a selection of a second transducer array layout map from the one or more associated transducer array layout maps.

At 1360, causing display of the first transducer array layout map and the second transducer array layout map. In some instances, composite data (e.g., a report, a plan, a summary, etc.) may be generated based on the first transducer array layout map and the second transducer array layout map. The composite data may include, for example, information associated with the first transducer array layout map and the second transducer array layout map and simulated electrical field distributions of the plurality of simulated electrical field distributions associated with the first transducer array layout map and the second transducer array layout map.

FIG. 14, shows a flowchart of a method 1400 for managing transducer array placement. One or more of the apparatus 100, the patient support system 602, the patient modeling application 608, the system 1000, and/or any other device/component described herein can be configured to perform a method 1300 comprising, at 1410, generating a three-dimensional (3D) model of a portion of the subject's body. Generating the 3D model may be based on image data from any modality of imaging, such as one or more images associated with CT, MRI, ultrasound, SPECT, x-ray CT, PET, a combination thereof, and/or the like. In some instances, one or more user devices may display a plurality of images of the portion of the subject's body. A selection of one or more images of the plurality of images may be received based on a region-of-interest (ROI), and a 3D model may be generated based on the one or more images. For example, an ROI may be based on features and/or structures within the one or more images, such as an enhancing tumor, a necrotic core, a resection cavity, craniotomy, and/or the like. In some instances receiving information associated with the ROI may be received from a first user device of the one or more user devices, and a selection of the one or more images may be received from a second user device of the one or more user device.

At 1420, determining, based on the 3D model and a plurality of simulated electrical field distributions, a plurality of transducer array layout maps. Determining the plurality of transducer array layout maps may include determining, based on the 3D model, a plurality of pairs of positions for transducer array placement. In some instances, the plurality of pairs of positions for transducer array placement may be determined from a library, record, corpus, and/or the like of standard transducer array layouts. In some instances, the plurality of pairs of positions for transducer array placement may be determined and/or selected to avoid one or more regions within the 3D model (e.g., avoidance regions, etc.), and/or the like. For each pair of positions of the plurality of pairs positions, a simulated electrical field distribution of the plurality of simulated electrical field distributions may be determined. Determining the simulated electrical field distribution for each pair of positions of the plurality of pairs positions may include simulating, at a first position of the pair of positions, a first electrical field generated by a first transducer array, and simulating, at a second position of the pair of positions, a second electrical field generated by a second transducer array. The second position may be opposite the first position. In some instances, a third electrical field generated by the first transducer array may be simulated at a third position, and a fourth electrical field generated by the second transducer array may be simulated at a fourth position opposite the third position, and, based on the third electrical field and the fourth electrical field, the simulated electrical field distribution may be determined. The simulated electrical field distribution may be determined based on the first electrical field and the second electrical field and/or the third electrical field and the fourth electrical field. The plurality of transducer array layout maps may be determined based on the plurality of simulated electrical field distributions.

At 1430, receiving a selection of a first transducer array layout map and a second transducer array layout map of the plurality of transducer array layout maps. The selection of the first transducer array layout map and the second transducer array layout map may be received via an interface of one or more user devices.

At 1430, determining, based on the first transducer array layout map and the second transducer array layout map, an overlap condition. Each transducer array layout map of the plurality of transducer array layout maps may include one or more pairs of positions of a plurality of pairs of positions for transducer array placement. The overlap condition may indicate that the first transducer array layout map comprises one or more pairs of positions of the plurality of pairs of positions that overlap one or more pairs of positions of the plurality of pairs of positions associated with the second transducer array layout map. For example, the first transducer array layout map may include positions for transducer arrays that are at the same position indicated on a 3D model (e.g., overlap, etc.) or the positions are at position indicated on a 3D model that satisfy a distance threshold and/or with in a tolerance positioning range relative to each other (e.g., substantially overlap, etc.).

At 1430, causing display of the overlap condition. One or more of the user device may be caused to display, for example via and interface, display, and/or the like, the overlap condition. In some cases, the overlap condition may be indicated by an audible sound and/or a notification.

In view of the described apparatuses, systems, and methods and variations thereof, herein below are described certain more particularly described embodiments of the invention. These particularly recited embodiments should not however be interpreted to have any limiting effect on any different claims containing different or more general teachings described herein, or that the "particular" embodiments are somehow limited in some way other than the inherent meanings of the language literally used therein.

Embodiment 1: A method comprising: generating a three-dimensional (3D) model of a portion of the subject's body, determining, based on the 3D model and a plurality of simulated electrical field distributions, a plurality of transducer array layout maps, determining, from the plurality of transducer array layout maps, one or more sets of transducer array layout maps, wherein each set of transducer array layout maps represents at least two transducer array layout maps with non-overlapping positions of a plurality of pairs of positions for transducer array placement, wherein the at least two transducer array layout maps satisfy a criterion, and causing display of the one or more sets of transducer array layout maps.

Embodiment 2: The embodiment as in any one of the preceding embodiments wherein the criterion comprises a magnitude of a simulated electric field distribution of the plurality of simulated electrical field distributions within a region-of-interest (ROI) associated with the 3D model, a power density associated with a simulated electric field distribution of the plurality of simulated electrical field distributions within the ROI, and an estimate of skin toxicity associated with the portion of the subject's body.

Embodiment 3: The embodiment as in any one of the preceding embodiments, further comprising receiving a selection of a set of transducer array layout maps of the one or more sets of transducer array layout maps.

Embodiment 4: The embodiment as in the embodiment 3, further comprising generating, based on the selected set of transducer array layout maps, composite data.

Embodiment 5: The embodiment as in the embodiment 4, wherein the composite data comprises information associated with the selected set of transducer array layout maps and simulated electrical field distributions of the plurality of simulated electrical field distributions associated with the selected set of transducer array layout maps.

Embodiment 6: The embodiment as in the embodiment 4, further comprising sending, to a user device, the composite data.

Embodiment 7: The embodiment as in any one of the preceding embodiments, wherein generating the 3D model comprises: causing one or more user devices to display a plurality of images of the portion of the subject's body, receiving, based on a region-of-interest (ROI), a selection of one or more images of the plurality of images, and generating, based on the one or more images, the 3D model.

Embodiment 8: The embodiment as in the embodiment 7, further comprising receiving, from a first user device of the one or more user devices, information associated with the ROI, and wherein receiving the selection of the one or more images comprises receiving the selection of the one or more images from a second user device of the one or more user devices.

Embodiment 9: The embodiment as in any one of the preceding embodiments, wherein determining the plurality of transducer array layout maps comprises: determining, based on the 3D model, the plurality of pairs of positions for transducer array placement, determining, for each pair of positions of the plurality of pairs positions, a simulated electrical field distribution of the plurality of simulated electrical field distributions, and determining, based on the plurality of simulated electrical field distributions, the plurality of transducer array layout maps.

Embodiment 10: The embodiment as in embodiment 9, wherein determining the simulated electrical field distribution for each pair of positions of the plurality of pairs positions comprises: simulating, at a first position of the pair of positions, a first electrical field generated by a first transducer array, simulating, at a second position of the pair of positions, a second electrical field generated by a second transducer array, wherein the second position is opposite the first position, and determining, based on the first electrical field and the second electrical field, the simulated electrical field distribution.

Embodiment 11: A method comprising: generating a three-dimensional (3D) model of a portion of the subject's body, determining, based on the 3D model and a plurality of simulated electrical field distributions, a plurality of transducer array layout maps, receiving a selection of a first transducer array layout map of the plurality of transducer array layout maps, wherein the first transducer array layout map satisfies a criterion, determining, from the plurality of transducer array layout maps, one or more associated transducer array layout maps, wherein each associated transducer array layout map comprises positions for transducer array placement that do not overlap positions for transducer array placement of the first transducer array layout map, wherein each associated transducer array layout map satisfies the criterion, receiving a selection of a second transducer array layout map from the one or more associated transducer array layout maps, and causing display of the first transducer array layout map and the second transducer array layout map.

Embodiment 12: The embodiment as in the embodiment 11, wherein the criterion comprises a magnitude of a simulated electric field distribution of the plurality of simulated electrical field distributions within a region-of-interest (ROI) associated with the 3D model, a power density associated with a simulated electric field distribution of the plurality of simulated electrical field distributions within the ROI, and an estimate of skin toxicity associated with the portion of the subject's body.

Embodiment 13: The embodiment as in any one of the embodiments 11-12, further comprising generating, based on the first transducer array layout map and the second transducer array layout map, composite data.

Embodiment 14: The embodiment as in the embodiment 13, wherein the composite data comprises information associated with the first transducer array layout map and the second transducer array layout map and simulated electrical field distributions of the plurality of simulated electrical field distributions associated with the first transducer array layout map and the second transducer array layout map.

Embodiment 15: The embodiment as in any one of the embodiments 11-14, wherein generating the 3D model comprises: causing one or more user devices to display a plurality of images of the portion of the subject's body, receiving, based on a region-of-interest (ROI), a selection of one or more images of the plurality of images, and generating, based on the one or more images, the 3D model.

Embodiment 16: The embodiment as in the embodiment 15, further comprising receiving, from a first user device of the one or more user devices, information associated with the ROI, and wherein receiving the selection of the one or more images comprises receiving the selection of the one or more images from a second user device of the one or more user devices.

Embodiment 17: The embodiment as in any one of the embodiments 11-16, wherein determining the plurality of transducer array layout maps comprises: determining, based on the 3D model, a plurality of pairs of positions for transducer array placement, determining, for each pair of positions of the plurality of pairs positions, a simulated electrical field distribution of the plurality of simulated electrical field distributions, and determining, based on the plurality of simulated electrical field distributions, the plurality of transducer array layout maps.

Embodiment 18: The embodiment as in the embodiment 17, wherein determining the simulated electrical field distribution for each pair of positions of the plurality of pairs positions comprises: simulating, at a first position of the pair of positions, a first electrical field generated by a first transducer array, simulating, at a second position of the pair of positions, a second electrical field generated by a second transducer array, wherein the second position is opposite the first position, and determining, based on the first electrical field and the second electrical field, the simulated electrical field distribution.

Embodiment 19: A method comprising: generating a three-dimensional (3D) model of a portion of the subject's body, determining, based on the 3D model and a plurality of simulated electrical field distributions, a plurality of transducer array layout maps, receiving a selection of a first transducer array layout map and a second transducer array layout map of the plurality of transducer array layout maps, determining, based on the first transducer array layout map and the second transducer array layout map, an overlap condition, and causing display of the overlap condition.

Embodiment 20: The embodiment as in the embodiment 19, wherein each transducer array layout map of the plurality of transducer array layout maps comprises one or more pairs of positions of a plurality of pairs of positions for transducer array placement, wherein the overlap condition indicates that the first transducer array layout map comprises one or more pairs of positions of the plurality of pairs of positions that overlap one or more pairs of positions of the plurality of pairs of positions associated with the second transducer array layout map.

Embodiment 21: A method comprising: presenting a plurality of images of an anatomic volume to at least one user; accepting, from the at least one user, a selection of which images of the anatomic volume should be used to generate the transducer array layouts; creating a model of electrical characteristics of the anatomic volume based on the selected images; determining a plurality of transducer array layouts; evaluating, based on the created model, which of the determined transducer array layouts satisfies at least one criterion; presenting, to the at least one user, a plurality of transducer array layouts that satisfy the at least one criterion; accepting, from the at least one user, a selection of one of the transducer array layouts that was presented to the at least one user; and generating a report that describes the selected transducer array layout.

Embodiment 22: The embodiment as in the embodiment 21, wherein the model of electrical characteristics of the anatomic volume is also based on at least one additional image.

Embodiment 23: The embodiment as in any one of the embodiments 21-22, wherein creating the model comprises performing segmentation based on input received from the at least one user.

Embodiment 24: The embodiment as in any one of the embodiments 21-23, wherein the at least one user comprises a first user and a second user, wherein the method further comprises (a) accepting an input from the first user identifying a region of interest, and (b) outputting data describing the region of interest to the second user.

Embodiment 25: The embodiment as in the embodiment 24, wherein creating the model comprises performing segmentation based on input received from the second user.

Embodiment 26: The embodiment as in any one of the embodiments 21-25, wherein the at least one user comprises a first user and a second user, wherein the method further comprises: accepting an input from the first user identifying a gross segmentation; and outputting data describing the gross segmentation to the second user.

Embodiment 27: The embodiment as in the embodiment 26, wherein creating the model comprises performing segmentation based on input received from the second user.

Embodiment 28: The embodiment as in any one of the embodiments 21-27, wherein the at least one user comprises a first user and a second user, wherein the method further comprises (a) accepting at least one note from the first user, and (b) outputting the at least one note to the second user.

Embodiment 29: The embodiment as in the embodiment 28, wherein creating the model comprises performing segmentation based on input received from the second user.

Embodiment 30: The embodiment as in any one of the embodiments 21-29, wherein the at least one user comprises a first user and a second user, wherein the method further comprises (a) accepting an input from the first user identifying an avoidance region, and (b) outputting data describing the avoidance region to the second user.

Embodiment 31: The embodiment as in the embodiment 30, wherein creating the model comprises performing segmentation based on input received from the second user.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is in no way intended that an order be inferred, in any respect. This holds for any possible non-express basis for interpretation, including: matters of logic with respect to arrangement of steps or operational flow; plain meaning derived from grammatical organization or punctuation; the number or type of embodiments described in the specification.

While the methods and systems have been described in connection with preferred embodiments and specific examples, it is not intended that the scope be limited to the particular embodiments set forth, as the embodiments herein are intended in all respects to be illustrative rather than restrictive.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is in no way intended that an order be inferred, in any respect. This holds for any possible non-express basis for interpretation, including: matters of logic with respect to arrangement of steps or operational flow; plain meaning derived from grammatical organization or punctuation; the number or type of embodiments described in the specification.

It will be apparent to those skilled in the art that various modifications and variations can be made without departing from the scope or spirit. Other embodiments will be apparent to those skilled in the art from consideration of the specification and practice disclosed herein. It is intended that the specification and examples be considered as exemplary only, with a true scope and spirit being indicated by the following claims.

What is claimed is:

1. A method comprising:
    generating a three-dimensional (3D) model of a portion of the subject's body;
    determining, based on the 3D model and a plurality of simulated electrical field distributions, a plurality of transducer array layout maps, each transducer array layout map comprising:
        a first pair of positions for placement of a first transducer array and a second transducer array; and
        a second pair of positions for placement of a first transducer array and a second transducer array;
    receiving a selection of a first transducer array layout map and a second transducer array layout map of the plurality of transducer array layout maps;
    determining, based on the first transducer array layout map and the second transducer array layout map, an overlap condition between the first and second array layout maps, wherein the overlap condition indicates that one or both of the first and second pairs of positions of the first transducer array layout map are at the same position indicated on the 3D model as one or both of the first and second pairs of positions of the second transducer array layout map; and
    causing display of the overlap condition.

2. The method of claim 1, wherein generating the 3D model comprises:
    causing one or more user devices to display a plurality of images of the portion of the subject's body;
    receiving, based on a region-of-interest (ROI), a selection of one or more images of the plurality of images; and
    generating, based on the one or more images, the 3D model.

3. The method of claim 2, further comprising receiving, from a first user device of the one or more user devices, information associated with the ROI, and wherein receiving the selection of the one or more images comprises receiving the selection of the one or more images from a second user device of the one or more user devices.

4. The method of claim 1, wherein determining the plurality of transducer array layout maps comprises:
determining, based on the 3D model, a plurality of pairs of positions for transducer array placement;
determining, for each pair of positions of the plurality of pairs positions, a simulated electrical field distribution of the plurality of simulated electrical field distributions; and
determining, based on the plurality of simulated electrical field distributions, the plurality of transducer array layout maps.

5. The method of claim 4, wherein determining the simulated electrical field distribution for each pair of positions of the plurality of pairs positions comprises:
simulating, at a first position of the pair of positions, a first electrical field generated by a first transducer array;
simulating, at a second position of the pair of positions, a second electrical field generated by a second transducer array, wherein the second position is opposite the first position; and
determining, based on the first electrical field and the second electrical field, the simulated electrical field distribution.

6. The method of claim 1, wherein causing display of the overlap condition comprises indicating the overlap condition on a user device by an audible sound, a notification, or both.

7. A method comprising:
generating a three-dimensional (3D) model of a portion of the subject's body;
determining, based on the 3D model and a plurality of simulated electrical field distributions, a plurality of transducer array layout maps, each transducer array layout map comprising:
a first pair of positions for placement of a first transducer array and a second transducer array; and
a second pair of positions for placement of a first transducer array and a second transducer array;
receiving a selection of a first transducer array layout map and a second transducer array layout map of the plurality of transducer array layout maps;
determining, based on the first transducer array layout map and the second transducer array layout map, an overlap condition between the first and second array layout maps, wherein the overlap condition indicates that one or both of the first and second pairs of positions of the first transducer array layout map are at substantially overlapping positions indicated on the 3D model as one or both of the first and second pairs of positions of the second transducer array layout map; and
causing display of the overlap condition.

8. The method of claim 7, wherein the overlap condition indicates that one or both of the first and second pairs of positions of the first transducer array layout map satisfy a distance threshold with respect to one or both of the first and second pairs of positions of the second transducer array layout map.

9. The method of claim 7, wherein the overlap condition indicates that one or both of the first and second pairs of positions of the first transducer array layout map are within a tolerance positioning range relative to one or both of the first and second pairs of positions of the second transducer array layout map.

10. A method, comprising:
presenting a plurality of images of an anatomic volume to at least one user;
accepting, from the at least one user, a selection of which images of the anatomic volume should be used to generate a plurality of transducer array layouts;
creating a model of electrical characteristics of the anatomic volume based on the selected images;
determining the plurality of transducer array layouts;
evaluating, based on the created model, which of the determined transducer array layouts satisfies at least one criterion;
presenting, to the at least one user, a plurality of transducer array layouts that satisfy the at least one criterion;
accepting, from the at least one user, a selection of one of the transducer array layouts that was presented to the at least one user; and
generating a report that describes the selected transducer array layout,
wherein the at least one user comprises a first user and a second user, wherein the method further comprises (a) accepting an input from the first user identifying a region of interest, and (b) outputting data describing the region of interest to the second user, and
wherein creating the model comprises, after outputting data describing the region of interest to the second user, performing segmentation based on input received from the second user regarding the region of interest.

11. The method of claim 10, wherein the model of electrical characteristics of the anatomic volume is also based on at least one additional image.

12. The method of claim 10, wherein creating the model comprises performing segmentation based on input received from the first user and the second user.

13. The method of claim 10, wherein the method further comprises: (a) accepting an input from the first user identifying a gross segmentation; and (b) outputting data describing the gross segmentation to the second user.

14. The method of claim 13, wherein creating the model comprises performing segmentation based on input received from the second user regarding the data describing the gross segmentation.

15. The method of claim 10, wherein the method further comprises (a) accepting at least one note from the first user, and (b) outputting the at least one note to the second user.

16. The method of claim 15, wherein creating the model comprises performing segmentation based on input received from the second user regarding the at least one note.

17. The method of claim 10, wherein the method further comprises (a) accepting an input from the first user identifying an avoidance region, and (b) outputting data describing the avoidance region to the second user.

18. The method of claim 17, wherein creating the model comprises performing segmentation based on input received from the second user regarding the data describing the avoidance region.

19. The method of claim 10, wherein the input received from the second user comprises segmentation information.

20. The method of claim 10, wherein the input received from the second user comprises guidance and/or instructions for determining and/or generating the plurality of transducer array layouts.

* * * * *